(12) United States Patent
Pepicelli et al.

(10) Patent No.: US 7,691,593 B2
(45) Date of Patent: Apr. 6, 2010

(54) REGULATION OF LUNG TISSUE BY PATCHED THERAPEUTICS AND FORMULATIONS AND USES RELATED THERETO

(75) Inventors: Carmen Pepicelli, Lowell, MA (US); Paula Lewis, Cambridge, MA (US); Andrew P. McMahon, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/727,195

(22) Filed: Dec. 3, 2003

(65) Prior Publication Data

US 2004/0171546 A1    Sep. 2, 2004

Related U.S. Application Data

(63) Continuation of application No. 09/394,020, filed on Sep. 10, 1999, now abandoned.

(60) Provisional application No. 60/099,952, filed on Sep. 11, 1998.

(51) Int. Cl.
*G01N 33/574* (2006.01)
*C12N 5/08* (2006.01)

(52) U.S. Cl. ............... 435/7.23; 435/371; 435/375; 800/10

(58) Field of Classification Search ............... None
See application file for complete search history.

(56) References Cited

U.S. PATENT DOCUMENTS

| | | | |
|---|---|---|---|
| 5,681,278 A | 10/1997 | Igo et al. | |
| 5,789,543 A | 8/1998 | Ingham et al. | |
| 5,837,538 A | 11/1998 | Scott et al. | |
| 6,027,882 A | 2/2000 | Scott et al. | |
| 6,165,747 A | 12/2000 | Ingham et al. | |
| 6,172,200 B1 | 1/2001 | Scott et al. | |
| 6,261,786 B1 * | 7/2001 | Marigo et al. | 435/7.1 |
| 6,271,363 B1 | 8/2001 | Ingham et al. | |
| 6,384,192 B1 | 5/2002 | Ingham et al. | |
| 6,429,354 B1 | 8/2002 | Scott et al. | |
| 6,432,970 B2 | 8/2002 | Beachy et al. | |
| 6,545,005 B1 | 4/2003 | Baxter et al. | |
| 6,551,782 B1 | 4/2003 | Scott et al. | |
| 6,552,016 B1 | 4/2003 | Baxter et al. | |
| 6,576,237 B1 | 6/2003 | Ingham et al. | |
| 6,607,913 B1 | 8/2003 | Ingham et al. | |
| 6,610,507 B2 | 8/2003 | Scott et al. | |
| 6,610,656 B1 | 8/2003 | Ingham et al. | |
| 6,613,798 B1 | 9/2003 | Porter | |
| 6,630,148 B1 | 10/2003 | Ingham et al. | |
| 6,664,075 B2 | 12/2003 | Ingham et al. | |
| 6,867,216 B1 | 3/2005 | Beachy et al. | |
| 6,884,775 B1 | 4/2005 | Tabin et al. | |
| 6,921,646 B2 | 7/2005 | Scott et al. | |
| 6,946,257 B1 | 9/2005 | Scott et al. | |
| 7,060,450 B1 | 6/2006 | Tabin et al. | |
| 7,144,732 B2 | 12/2006 | Ingham et al. | |
| 7,445,778 B2 | 11/2008 | Burkly et al. | |
| 2002/0015702 A1 | 2/2002 | Burkly et al. | |
| 2003/0022819 A1 | 1/2003 | Ling et al. | |
| 2003/0186309 A1 | 10/2003 | Scott et al. | |
| 2004/0060568 A1 | 4/2004 | Dudek et al. | |
| 2004/0110663 A1 | 6/2004 | Dudek et al. | |
| 2005/0002933 A1 | 1/2005 | Baron et al. | |
| 2005/0054568 A1 | 3/2005 | Ling et al. | |

FOREIGN PATENT DOCUMENTS

| | | |
|---|---|---|
| WO | WO-95/18856 | 7/1995 |
| WO | WO-95/23223 | 8/1995 |
| WO | WO-96/17924 | 6/1996 |
| WO | WO-98/35020 | 8/1998 |
| WO | WO-99/20298 | 4/1999 |
| WO | WO 99/52534 A1 | 10/1999 |
| WO | WO-00/18428 | 4/2000 |
| WO | WO-01/98344 A2 | 12/2001 |
| WO | WO-02/30462 | 4/2002 |

OTHER PUBLICATIONS

Fujita et al, 1997, Biochemical and Biophysical Research Communications, 238: 658-665.*
Stecca et al, 2002, Journal of Biology. 1(9):1-4.*
Warburton et al 2000. Mechanisms of Development. 92: 55-81.*
Kumar et al. 2004. Frontiers in Bioscience. 9: 464-480.*
Ballard, 1991. Endocrinology. 128(6): 2916-24.*
Yang, 1991. Exp Lung Res. 15(4): 527-35.*
Schwede et al. Pharmacology & Therapeutics. 2000. 199-226.*
Wang et al. (Nuc. Acids Res. 27: 4609-4618, 1999; p. 4617.*
Kaufman et al (Blood 94: 3178-3184, 1999.*
Wigley et al. Reprod Fed Dev 6: 585-588, 1994.*
Campbell et al. Theriology 47(1): 63-72, 1997.*

(Continued)

*Primary Examiner*—Bridget E Bunner
*Assistant Examiner*—Zachary C Howard
(74) *Attorney, Agent, or Firm*—Ropes & Gray LLP

(57) ABSTRACT

The present application relates to a method for modulating the growth state of an lung tissue, or a cell thereof, e.g., by ectopically contacting the tissue, in vitro or in vivo, with a hedgehog therapeutic, a ptc therapeutic, or an FGF-10 therapeutic in an amount effective to alter the rate (promote or inhibit) of proliferation of cells in the lung tissue, e.g., relative to the absence of administration of the hedgehog therapeutic or ptc therapeutic. The subject method can be used, for example, to modulate the growth state of epithelial and/or mesenchymal cells of a lung tissue, such as may be useful as part of a regimen for prevention of a disease state, or in the treatment of an existing disease state or other damage to the lung tissue.

3 Claims, 5 Drawing Sheets

OTHER PUBLICATIONS

Figure 1A:
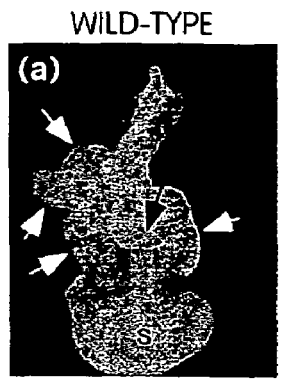
Figure 1D:
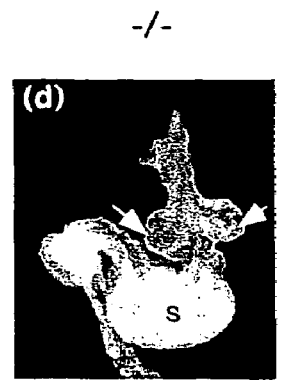

Cardoso et al (1996. Developmental Dynamics. 207: 47-59).*
Schuger et al (1993. Developmental Biology. 159: 462-473).*
Watkins et al, 2003. Nature. 422: 313-317.*
Yuan et al, 2007. Oncogene. 26: 1046-1055.*
Bellusci et al., "Fibroblast Growth Factor 10 (FGF 10) and Branching Morphogenesis in the Embryonic Mouse Lung" Development, 124:4867-4878 (1997).
Bellusci et al., "Involvement of Sonic Hedgehog (Shh) in Mouse Embryonic Lung growth and Morphogenesis," Development 124:53-63 (1997).
Hammerschmidt et al., "The World According to Hedgehog," Trends in Genet. 13(1):14-21 (1997).
Min et al. "Fgf-10 is Required for Both Limb and Lung Development and Exhibits Striking Functional Similarity to Drosophila Branchless," Genes & Devel. 12:3156-3161 (1998).
Olech et al., "Role of Basic Fibroblast Growth Factor in Revascularization of Rabbit Tracheal Autografts," Annals Thoracic Surg. 52(2)258-262 (1991).
Fujita et al., "Involvement of Sonic Hedgehog in the Cell Growth of LK-2 Cells, Human Lung Squamous Carcinoma Cells," Biochemical and Biophysical Research Communications 238:658-664(1997).
Litingtung, et al., "Sonic hedgehog is essential to foregut development," Nature Genetics, vol. 20(1), pp. 58-61 (1998).

* cited by examiner

WILD-TYPE

-/-

WILD-TYPE

-/-

WILD-TYPE

-/-

WILD-TYPE

-/-

WILD-TYPE

-/-

*Ptc-1*

*Ptc-2*

*Gli-1*

*Gli-2*

*Gli-2*

REGULATION OF LUNG TISSUE BY PATCHED THERAPEUTICS AND FORMULATIONS AND USES RELATED THERETO

RELATED APPLICATIONS

This application is a continuation of U.S. patent application Ser. No. 09/394,020, filed on Sep. 10, 1999, now abandoned, which claims priority to U.S. Provisional Patent Application Ser. No. 60/099,952, filed Sep. 11, 1998, the specifications of each of which are incorporated by reference herein in their entirety.

GOVERNMENT FUNDING

Certain work described herein was funded by the National Institutes of Health Grant No. NS33642. The government may have rights in inventions described herein.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185-199).

Members of the Hedgehog family of signaling molecules mediate many important short- and long-range patterning processes during invertebrate and vertebrate development. In the fly a single hedgehog gene regulates segmental and imaginal disc patterning. In contrast, in vertebrates a hedgehog gene family is involved in the control of left-right asymmetry, polarity in the CNS, somites and limb, organogenesis, chondrogenesis and spermatogenesis.

The first hedgehog gene was identified by a genetic screen in the fruitfly *Drosophila melanogaster* (Nüsslein-Volhard, C. and Wieschaus, E. (1980) *Nature* 287, 795-801). This screen identified a number of mutations affecting embryonic and larval development. In 1992 and 1993, the molecular nature of the *Drosophila* hedgehog (hh) gene was reported (CF, Lee et al. (1992) *Cell* 71, 33-50), and since then, several hedgehog homologues have been isolated from various vertebrate species. While only one hedgehog gene has been found in *Drosophila* and other invertebrates, multiple Hedgehog genes are present in vertebrates.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al. (1992) *Genes Dev.* 2635-2645; Chang, D. E. et al. (1994) *Development* 120:3339-3353), Hedgehog precursor proteins undergo an internal autoproteolytic cleavage which depends on conserved sequences in the C-terminal portion (Lee et al. (1994) *Science* 266:1528-1537; Porter et al. (1995) *Nature* 374:363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294-2303; Porter et al. (1995) supra; Ekker, S. C. et al. (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al. (1995) *Development* 121:2537-2547; Roelink, H. et al. (1995) *Cell* 81:445-455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the HH precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short and long range Hedgehog signaling activities in *Drosophila* and vertebrates (Porter et al. (1995) supra; Ekker et al. (1995) supra; Lai et al. (1995) supra; Roelink, H. et al. (1995) *Cell* 81:445-455; Porter et al. (1996) supra; Fietz, M. J. et al. (1995) *Curr. Biol.* 5:643-651; Fan, C.-M. et al. (1995) *Cell* 81:457-465; Mart', E., et al. (1995) *Nature* 375:322-325; Lopez-Martinez et al. (1995) *Curr. Biol* 5:791-795; Ekker, S. C. et al. (1995) *Development* 121:2337-2347; Forbes, A. J. et al.(1996) *Development* 122: 1125-1135).

HH has been implicated in short- and longe range patterning processes at various sites during *Drosophila* development. In the establishment of segment polarity in early embryos, it has short range effects which appear to be directly mediated, while in the patterning of the imaginal discs, it induces long range effects via the induction of secondary signals.

In vertebrates, several hedgehog genes have been cloned in the past few years (see Table 1). Of these genes, Shh has received most of the experimental attention, as it is expressed in different organizing centers which are the sources of signals that pattern neighbouring tissues. Recent evidence indicates that Shh is involved in these interactions.

The interaction of a hedgehog protein with one of its cognate receptor, patched, sets in motion a cascade involving the activation and inhibition of downstream effectors, the ultimate consequence of which is, in some instances, a detectable change in the transcription or translation of a gene. Transcriptional targets of hedgehog signaling are the patched gene itself (Hidalgo and Ingham, 1990 *Development* 110, 291-301;

Marigo et al., 1996) and the vertebrate homologs of the *drosophila* cubitus interruptus (Ci) gene, the GLI genes (Hui et al. (1994) *Dev Biol* 162:402-413). Patched gene expression has been shown to be induced in cells of the limb bud and the neural plate that are responsive to Shh. (Marigo et al. (1996) *Development* 122:1225-1233). The GLI genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the GLI gene has been reported to be upregulated in response to hedgehog in limb buds, while transcription of the GLI3 gene is downregulated in response to hedgehog induction (Marigo et al. (1996) *Development* 122:1225-1233). Moreover, it has been demonstrated that elevated levels of Ci are sufficient to activate patched (ptc) and other hedgehog target genes, even in the absence of hedgehog activity.

SUMMARY OF THE INVENTION

One aspect of the present application relates to a method for modulating the growth state of an lung tissue, or a cell thereof, e.g., by ectopically contacting the tissue, in vitro or in vivo, with a hedgehog therapeutic, a ptc therapeutic, or an FGF-10 therapeutic (described infra) in an amount effective to alter the rate (promote or inhibit) of proliferation of cells in the lung tissue, e.g., relative to the absence of administeration of the hedgehog therapeutic or ptc therapeutic. The subject method can be used, for example, to modulate the growth state of epithelial and/or mesenchymal cells of a lung tissue, such as may be useful as part of a regimen for prevention of a disease state, or in the treatment of an existing disease state or other damage to the lung tissue.

Wherein the subject method is carried out using a hedgehog therapeutic, the hedgehog therapeutic preferably a polypeptide including a hedgehog portion comprising at least a bioactive extracellular portion of a hedgehog protein, e.g., the hedgehog portion includes at least 50, 100 or 150 (contiguous) amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In certain preferred embodiments, the hedgehog portion has an amino acid sequence at least 60, 75, 85, or 95 percent identical with a hedgehog protein of any of SEQ ID Nos. 10-18 or 20, though sequences identical to those sequence listing entries are also contemplated as useful in the present method. The hedgehog portion can be encoded by a nucleic acid which hybridizes under stringent conditions to a nucleic acid sequence of any of SEQ ID Nos. 1-9 or 19, e.g., the hedgehog portion can be encoded by a vertebrate hedgehog gene, especially a human hedgehog gene.

In certain embodiments, the hedgehog polypeptide is modified with one or more sterol moieties, e.g., cholesterol or a derivative thereof.

In certain embodiments, the hedgehog polypeptide is modified with one or more fatty acid moieties, such as a fatty acid moiety selected from the group consisting of myristoyl, palmitoyl, stearoyl, and arachidoyl.

In other embodiments, the subject method can be carried out by administering a gene activation construct, wherein the gene activation construct is deigned to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent, In yet other embodiments, the subject method can be carried out using a ptc therapeutic. An exemplary ptc therapeutic is a small organic molecule which binds to a patched protein and derepresses patched-mediated inhibition of mitosis, e.g., a molecule which binds to patched and mimics hedgehog-mediated patched signal transduction, which binds to patched and regulates patched-dependent gene expression. For instance, the binding of the ptc therapeutic to patched may result in upregulation of patched and/or gli expression.

In a more generic sense, the ptc therapeutic can be a small organic molecule which induces hedgehog-mediated patched signal transduction, such as by altering the localization, protein-protein binding and/or enzymatic activity of an intracellular protein involved in a patched signal pathway. For instance, the ptc therapeutic may alter the level of expression of a hedgehog protein, a patched protein or a protein involved in the intracellular signal transduction pathway of patched.

In certain embodiments, the ptc therapeutic is an antisense construct which inhibits the expression of a protein which is involved in the signal transduction pathway of patched and the expression of which antagonizes hedgehog-mediated signals. The antisense construct is preferably an oligonucleotide of about 20-30 nucleotides in length and having a GC content of at least 50 percent.

In other embodiments, the ptc therapeutic is an inhibitor of protein kinase A (PKA), such as a 5-isoquinolinesulfonamide. The PKA inhibitor can be a cyclic AMP analog. Exemplary PKA inhibitors include N-[2-((p-bromocinnamyl)amino)ethyl]-5-isoquinolinesulfonamide, 1-(5-isoquinolinesulfonyl)-2-methylpiperazine, KT5720, 8-bromo-cAMP, dibutyryl-cAMP and PKA Heat Stable Inhibitor isoform α. Another exemplary PKA inhibitor is represented in the general formula:

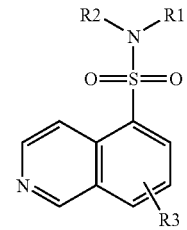

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—R$_8$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_8$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—S—$(CH_2)_m$—$R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

The subject method can be used to prevent or treat various lung diseases, to control wound healing or other reformation processes in lung, and to augment lung transplantation.

Wherein the subject method is carried out using an fgf-10 therapeutic, the fgf-10 therapeutic preferably a polypeptide including a fgf-10 portion comprising at least a bioactive extracellular portion of a fgf-10 protein, e.g., the fgf-10 portion includes at least 50, 100 or 150 (contiguous) amino acid residues of a fgf-10 protein, preferably a human fgf-10 protein such as shown in SEQ ID No. 24.

In certain preferred embodiments, the fgf-10 portion has an amino acid sequence at least 60, 75, 85, or 95 percent identical with the fgf-10 protein of SEQ ID No. 24, though a sequence identical with SEQ ID No. 24 is also contemplated as useful in the present method. The fgf-10 portion can be encoded by a nucleic acid which hybridizes under stringent conditions to a nucleic acid sequence of SEQ ID No. 23, e.g., the fgf-10 portion can be encoded by a vertebrate fgf-10 gene, especially a human fgf-10 gene.

In other embodiments, the subject method can be carried out by administering a gene activation construct, wherein the gene activation construct is deigned to recombine with a genomic fgf-10 gene of the patient to provide a heterologous transcriptional regulatory sequence operatively linked to a coding sequence of the fgf-10 gene.

In still other embodiments, the subject method can be practiced with the administration of a gene therapy construct encoding a fgf-10 polypeptide. For instance, the gene therapy construct can be provided in a composition selected from a group consisting of a recombinant viral particle, a liposome, and a poly-cationic nucleic acid binding agent, Yet another aspect of the present invention concerns preparations of a hedgehog, ptc or fgf-10 therapeutic formulated for application to lung tissue, e.g., by aerosol. For example, such formulations may include a polypeptide comprising a hedgehog polypeptide sequence including a bioactive fragment of a hedgehog protein, which polypeptide is formulated for application to lung tissue by inhalation.

DETAILED DESCRIPTION OF THE INVENTION

FIG. 1. Morphology and epithelial phenotype of Shh -/- mouse lungs. (A) At 12.5 dpc, the wt mouse lung has branched several times to give rise to distinct lobes (arrows). (B) Trachea and esophagus are separate tubes. (C) Cross-section at the level of the lung shows branching and lobation. (D) At 12.5 dpc, Shh-deflcient lungs have failed to undergo lobation or subsequent extensive branching. (E) Trachea and esophagus remain fused at the tracheoesophageal septum. (F) Mutant lungs have branched only once. (G) At 18.5 dpc, airsac formation is in progress in the wt and the respiratory surface is in tight association with blood vessels. (H) There is little branching or growth of the poorly vascularized mutant lungs, but airsac formation at the distal epithelial tips is apparent (arrows). (I) By 18.5 dpc, wild-type lungs have estab- lished the conducting airways and respiratory bronchioles, alveolar formation is in progress. (J) In contrast, in a mutant lung of the same stage, branching is dramatically decreased. Only a few primary branches (arrows) and air sacs (arrowheads) are present. (K) In the wild-type, trachea and esophagus are separated. The trachea is lined by columnar cells, the esophagus by stratified epithelium. (L) Air sacs are made of cuboidal cells. (M) In the mutant, trachea and esophagus are fused to form a fistula. Differentiation into columnar and stratified epithelium is apparent, (N) as is the characteristic cuboidal epithelium of the air sacs. Demarcation lines between terminal bronchioles and respiratory surface are indicated. (O) Proximal lung epithelium of the 18.5 dpc wt lung expresses CCSP in Clara cells, and (P) SP-C in type II pneumocytes of the distal epithelium. (Q) CCSP and (R) SP-C are expressed in the correct proximo-distal domain in the mutant. Bars denote 1 mm (G, H only) or 10μm. (A, D, G, H) are ventral views, all others transverse sections. Abbreviations: t—trachea, e—esophagus, l—lung, h—heart, s—stomach, mb—mainstem bronchus, b—bronchus, tb—terminal bronchiole, a—air sac.

FIG. 2. In situ analysis of gene expression in the lungs of Shh mutants. Expression of the genes indicated was investigated in whole mount vibratome sections through lungs removed from wt 11.5 (left panel) and 12.5 dpc (center panel), and Shh-mutant 12.5 dpc (right panel) embryos. FIGS. 2A to 2K each shows the expression of: (A) Ptc-1; (B) Pct-2; (C) Gli-1; (D) Gli-2; (E) Gli -2; (F) Bmp-4; (G) Wnt-7b; (H) Wnt-2; (I) FGF-R2; (J) FGF-10; and (K) Nkx-2.1.

Figure 3A:
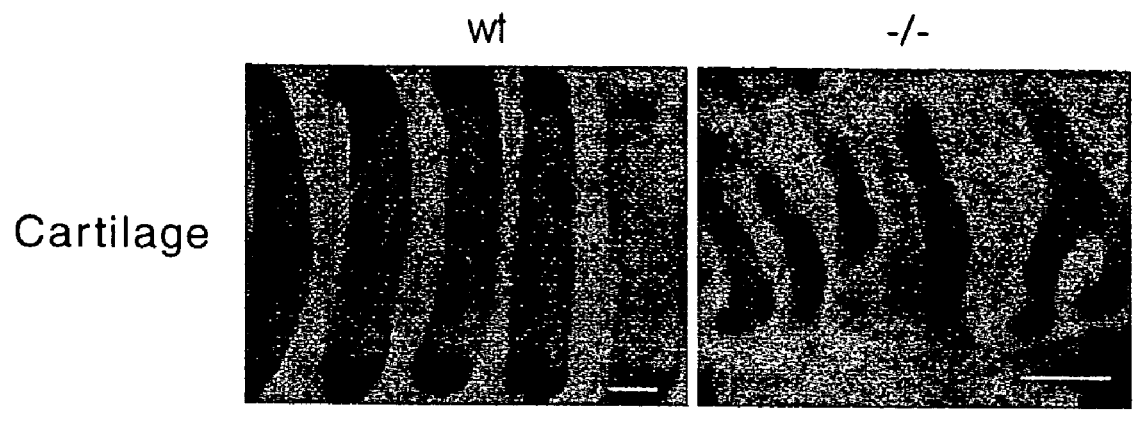

FIG. 3. Mesenchyme differentiation at 18.5 dpc. (a) Both wt and mutant lungs display cartilaginous rings around the trachea as indicated by alcian-blue staining. (b) While in the wild-type lung a layer of smooth muscle surrounds the conducting epithelium, the mutant lung mesenchyme does not differentiate into muscle (right panel). Bars denote 10 mm

DETAILED DESCRIPTION OF THE INVENTION

Development of the lung, through a process known as branching morphogenesis, is strictly dependent on interactions between endodermally derived epithelial cells and the splanchnic mesenchyme. Cell-cell interactions form the functional basis for branching morphogenesis and occur through the activity of a number of mediators, including the extracellular matrix, cellular receptors, and morphogenetic signaling molecules such as peptide growth factors. The molecular regulatory signals and in particular the role of transcriptional factors in branching morphogenesis and lung injury/repair are an important source of information for the treatment of injury. Furthermore, because the lungs continue to undergo development after birth, untimely activation of alternative morphogenetic signals released by tissue injury or repair or both may potentially derail normal morphogenesis and result in structural and functional aberrations characteristic of neonatal lung disease.

It is demonstrated herein that hedgehog proteins, such as Shh, is essential for development of the respiratory system. In Shh null mutants, for example, the trachea and esophagus do not separate properly and the lungs form a rudimentary sac due to failure of branching and growth after formation of the primary lung buds. Interestingly, normal proximo-distal differentiation of the airway epithelium occurs, indicating that Shh is not needed for differentiation events. In addition, the transcription of several mesenchymally expressed downstream targets of Shh is abolished. These results highlight the importance of epithelially derived Shh in regulating branching morphogenesis of the lung, and establish a role for hedgehog in lung morphogenesis, disease and repair, and suggest that SHH normally regulates lung mesenchymal cell proliferation in vivo.

I. Overview

The present application is directed to the discovery that preparations of hedgehog polypeptides can be used to control the formation and/or maintenance of lung tissue. As described in the appended examples, hedgehog proteins are implicated in the proliferation and differentiation of lung mesenchymal and epithelial cells and provide early signals that regulate the formation and maintenance of lung tissues. The present invention provides a method for regulating the growth state of lung tissue, e.g., either in vitro or in vivo. In general, the method of the present invention comprises contacting lung tissue, or cells derived therefrom, with an amount of a hedgehog therapeutic (defined infra) which produces a non-toxic response by the cell of induction or inhibition of the formation of lung tissue microarchetecture, e.g., depending on the whether the hedgehog therapeutic is a sufficient hedgehog agonist or hedgehog antagonist. The subject method can be carried out on lung cells which may be either dispersed in culture or a part of an intact tissue or organ. Moreover, the method can be performed on cells which are provided in culture (in vitro), or on cells in a whole animal (in vivo).

Without wishing to be bound by any particular theory, the ability of hedgehog proteins to regulate the growth state of lung tissue may be due at least in part to the ability of these proteins to antagonize (directly or indirectly) patched-mediated regulation of gene expression and other physiological effects mediated by that protein. The patched gene product, a cell surface protein, is understood to signal through a pathway which causes transcriptional repression of members of the Wnt and Dpp/BMP families of morphogens, proteins which impart positional information. In development of the CNS and patterning of limbs in vertebrates, the introduction of hedgehog relieves (derepresses) this inhibition conferred by patched, allowing expression of particular gene programs.

Recently, it has been reported that mutations in the human version of patched, a gene first identified in a fruit fly developmental pathway, cause a hereditary skin cancer and may contribute to sporadic skin cancers. See, for example, Hahn et al. (1996) Cell 86:841-851; and Johnson et al. (1996) Science 272:1668-1671. The demonstration that nevoid basal-cell carcinoma (NBCC) results from mutations in the human patched gene provided an example of the roles patched plays in post-embryonic development. These observations have led the art to understand one activity of patched to be a tumor suppressor gene, which may act by inhibiting proliferative signals from hedgehog. Our observations set forth below reveal potential new roles for the hedgehog/patched pathway in maintenance of proliferation and differentiation of lung tissue. Accordingly, the present invention contemplates the use of other agents which are capable of mimicking the effect of the hedgehog protein on patched signaling, e.g., as may be identified from the drug screening assays described below.

Moreover, we demonstrate that fgf-10 is an important component of the hedgehog regulatory network present in the embryonic lung, controlling proliferation, differentiation and pattern formation. Accordingly, Applicants contemplate that agonists and antagonist of fgf-10 activity.

II. Definitions

For convenience, certain terms employed in the specification, examples, and appended claims are collected here.

The term "hedgehog therapeutic" refers to various forms of hedgehog polypeptides, as well as peptidomimetics, which can modulate the proliferation/differentiation state of lung cells by, as will be clear from the context of individual examples, mimicing or potentiating (agonizing) or inhibiting (antagonizing) the effects of a naturally-occurring hedgehog protein. A hedgehog therapeutic which mimics or potentiates the activity of a wild-type hedgehog protein is a "hedgehog agonist". Conversely, a hedgehog therapeutic which inhibits the activity of a wild-type hedgehog protein is a "hedgehog antagonist".

In particular, the term "hedgehog polypeptide" encompasses preparations of hedgehog proteins and peptidyl fragments thereof, both agonist and antagonist forms as the specific context will make clear.

As used herein the term "bioactive fragment of a hedgehog protein" refers to a fragment of a full-length hedgehog polypeptide, wherein the fragment specifically agonizes or antagonizes inductive events mediated by wild-type hedgehog proteins. The hedgehog biactive fragment preferably is a soluble extracellular portion of a hedgehog protein, where solubility is with reference to physiologically compatible solutions. Exemplary bioactive fragments are described in PCT publications WO 95/18856 and WO 96/17924.

The term "patched" or "ptc" refers to a family of related transmembrane proteins which have been implicated in the signal transduction induced by contacting a cell with a hedgehog protein. For example, the mammalian ptc family includes ptc1 and ptc2. In addition to references set out below, see also Takabatake et al. (1997) FEBS Lett 410:485 and GenBank AB000847 for examples of ptc2. Unless otherwise evident from the context, it will be understood that embodiments described in the context of ptc1 (or just ptc) also refer to equivalent embodiments involving otherptc homologs like ptc2.

The term "ptc therapeutic" refers to agents which either (i) mimic the effect of hedgehog proteins on patched signalling, e.g., which antagonize the cell-cycle inhibitory activity of patched, or (ii) activate or potentiate patched signalling. In other embodiments, the ptc therapeutic can be a hedgehog antagonist. The ptc therapeutic can be, e.g., a peptide, a nucleic acid, a carbohydrate, a small organic molecule, or natural product extract (or fraction thereof).

The term "fgf-10 therapeutic" refers to agents which mimic or antagonize, as appropriate, the effect of fgf-10 proteins on proliferation and differentiation of lung tissue. Such agents also include small organic molecules which bind to the fgf-10 receptor and either inhibit or agonize fgf-10 signalling.

A "proliferative" form of a ptc, hedgehog or fgf-10 therapeutic is one which induces proliferation of lung cells, e.g., directly or indirectly, mesenchymal or epithelial cells. Conversely, an "antiproliferative" form of a ptc, hedgehog or fgf-10 therapeutic is one which inhibits proliferation of lung cells, preferably in a non-toxic manner, e.g., by promoting or maintaining a differentiated phenotype or otherwise promoting quiescence.

By way of example, though not wishing to be bound by a particular theory, proliferative hedgehog polypeptide will generally be a form of the protein which derepresses patched-mediated cell-cycle arrest, e.g., the polypeptide mimics the effect of a naturally occurring hedgehog protein effect on lung tissues. A proliferative ptc therapeutic includes other agents which depress patched-mediated cell-cycle arrest, and may act extracellularly or intracellularly.

An illustrative antiproliferative ptc therapeutic agent may potentiate patched-mediated cell-cycle arrest. Such agents can be small molecules that inhibit, e.g., hedgehog binding to patched, as well as agents which stimulate and/or potentiate a signal transduction pathway of the patched protein.

As used herein, "proliferating" and "proliferation" refer to cells undergoing mitosis.

As used herein, "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

A "patient" or "subject" to be treated by the subject method can mean either a human or non-human animal.

An "effective amount" of, e.g., a hedgehog therapeutic, with respect to the subject method of treatment, refers to an amount of, e.g., a hedgehog polypeptide in a preparation which, when applied as part of a desired dosage regimen brings about a change in the rate of cell proliferation and/or the state of differentiation of a cell so as to produce (or inhibit as the case may be) proliferation of lung cells in an amount according to clinically acceptable standards for the disorder to be treated or the cosmetic purpose.

The "growth state" of a cell refers to the rate of proliferation of the cell and the state of differentiation of the cell.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a hedgehog sequence disclosed herein.

The term "corresponds to", when referring to a particular polypeptide or nucleic acid sequence is meant to indicate that the sequence of interest is identical or homologous to the reference sequence to which it is said to correspond.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$—$(hh)_m$—$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

III. Exemplary Applications of Method and Compositions

The subject method has wide applicability to the treatment or prophylaxis of disorders afflicting lung tissue, as well as in in vitro cultures. In general, the method can be characterized as including a step of administering to an animal an amount of a ptc, hedgehog or fgf-10 therapeutic effective to alter the growth state of a treated lung tissue. The mode of administration and dosage regimens will vary depending on the phenotype of, and desired effect on the target lung tissue. Likewise, as described in further detail below, the use of a particular ptc, hedgehog or fgf-10 therapeutic, e.g., an agonist or antagonist, will depend on whether proliferation of cells in the treated lung tissue is desired or intended to be prevented.

In one aspect, the present invention provides pharmaceutical preparations and methods for controlling the proliferation of lung tissue utilizing, as an active ingredient, a hedgehog polypeptide or a mimetic thereof. The invention also relates to methods of controlling proliferation of mesenchymal and epithelial cells of the tissue by use of the pharmaceutical preparations of the invention.

The formulations of the present invention may be used as part of regimens in the treatment of disorders of, surgical repair of, or transplantation of lung tissues and whole organs. The methods and compositions disclosed herein also provide for the treatment of a variety of proliferative cancerous disorders effecting lung tissue. For instance, the subject method can be used to control wound healing processes, as for example may be desirable in connection with any surgery involving lung tissue.

In certain embodiments, the subject compositions can be used to inhibit, rather than promote, growth of lung-derived tissue. For instance, certain of the compositions disclosed herein may be applied to the treatment or prevention of a variety hyperplastic or neoplastic conditions. The method can find application for the treatment or prophylaxis of, e.g., used to inhibit the growth and metastasis of lung cancer cells. For instance, inhibitory forms of the subject ptc, hedgehog and fgf-10 therapeutics may be used as part of a treatment program for small cell lung cancer (SCLC), as well as non-small cell lung cancer (NSCLC), such as adenocarcinoma, lung cell carcinoma and sguamous cell carcinoma.

In other embodiments, the subject method can be used to treat rheumatoid lung disease, which may be marked by pleural thickening, adhesions, and pleural effusions. Such lung (pulmonary) manifestations can occur in both adult and juvenile forms of rheumatoid arthritis.

In other embodiments, the subject method can be used to treat, or lessen the severity of, damage to lung tissue as a complication of respiratory diseases such as broncho-pneumonia, chronic bronchitis, cystic fibrosis and asthma, and bronchospasm, or other apical interstitial lung diseases, such as cystic fibrosis, ankylosing spondylitis, sarcoidosis, silicosis, eosinophlic granuloma, tuberculosis, and lung infections.

In certain embodiments, the subject method can be used to treat or prevent damage to lung tissue resulting from allergic rhinitis, asthma, emphysema, chronic bronchitis, pneumoconiosis, respiratory distress syndrome, idiopathic pulmonary fibrosis and primary pulmonary hypertension The subject method can be used in the treatment or prevention of occupational lung disease such as asbestos-related diseases, silicosis, occupational asthma, coal worker's pneumoconiosis, berylliosis, and industrial bronchitis.

In still other embodiments, the subject method can be used to treat certain health consequences of smoking which may result in degeneration of lung tissue.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

Still another aspect of the present invention provides a method of stimulating the growth and regulating the differentiation of epithelial tissue in tissue culture.

In one embodiment, the subject method can be used to regulate the proliferation and/or differentiation of lung mesenchymal progenitor cells.

The maintenance of lung tissues and whole organs ex vivo is also highly desirable. Lung and heart-lung transplantation therapy is well established in the treatment of certain human disease. The subject method can be used to maintain the tissue structure of lung tissue ex vivo, and in certain embodiments to accelerate the growth of certain lung tissue in vitro. The present method can also be used for improving the "take rate" of a lung transplants in vivo.

IV. Exemplary Hedgehog Therapeutic Compounds.

The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject therapeutics can be derived are characterized by a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al. (1992) *Genes Dev.* 2635-2645; Chang, D. E. et al. (1994) *Development* 120:3339-3353), hedgehog precursor proteins naturally undergo an internal autoproteolytic cleavage which depends on conserved sequences in the C-terminal portion (Lee et al. (1994) *Science* 266:1528-1537; Porter et al. (1995) *Nature* 374:363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A., et al. (1995) *Mol Cell. Biol* 15:2294-2303; Porter et al (1995) supra; Ekker, S. C. et al (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al. (1995) *Development* 121:2537-2547; Roelink, H. et al. (1995) *Cell* 81:445-455). Cell surface retention of the N-terminal peptide is dependent on autocleavage, as a truncated form of hedgehog encoded by an RNA which terminates precisely at the normal position of internal cleavage is diffusible in vitro (Porter et al (1995) supra) and in vivo (Porter, J. A. et al. (1996) *Cell* 86, 21-34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single *drosophila* hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth members herein referred to as tiggie-winkle hedgehog (Thh), appears specific to fish. According to the appended sequence listing, (see also Table 1) a chicken Shh polypeptide is encoded by SEQ ID No: 1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No. 8; and a zebrafish Thh is encoded by SEQ ID No. 9.

TABLE 1

Guide to hedgehog sequences in Sequence Listing

|  | Nucleotide | Amino Acid |
| --- | --- | --- |
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| Drosophila HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19kDa fragment corresponding to an proteolytic N-terminal portion of the mature protein.

In addition to proteolytic fragmentation, the vertebrate hedgehog proteins can also be modified post-translationally, such as by glycosylation and/or addition of lipophilic moieties, such as stents, fatty acids, etc., though bacterially produced (e.g. unmodified) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

There are a wide range of lipophilic moieties with which hedgehog polypeptides can be derivatived. The term "lipophilic group", in the context of being attached to a hedgehog polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, sterols, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

In one embodiment, the hedgehog polypeptide is modified with one or more sterol moieties, such as cholesterol. See, for example, PCT publication WO 96/17924. In certain embodiments, the cholesterol is preferably added to the C-terminal glycine were the hedgehog polypeptide corresponds to the naturally-occurring N-terminal proteolytic fragment.

In another embodiment, the hedgehog polypeptide can be modified with a fatty acid moiety, such as a myrostoyl, palmitoyl, stearoyl, or arachidoyl moiety. See, e.g., Pepinsky et al. (1998) *J Biol. Chem* 273: 14037.

In addition to those effects seen by cholesterol-addition to the C-terminus or fatty acid addition to the N-terminus of extracellular fragments of the protein, at least certain of the biological activities of the hedgehog gene products can potentiated by derivativation of the protein with lipophilic moieties at other sites on the protein and/or by moieties other than cholesterol or fatty acids. Certain aspects of the invention are directed to the use of preparations of hedgehog polypeptides which are modified at sites other than N-terminal or C-terminal residues of the natural processed form of the protein, and/or which are modified at such terminal residues with lipophilic moieties other than a sterol at the C-terminus or fatty acid at the N-terminus.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1-C18)-alkyl phosphate diesters, —O—CH2—CH(OH)—O—(C12-C18)-alkyl, and in particular conjugates with pyrene derivatives. The lipophilic moiety can be a lipophilic dye suitable for use in the invention include, but are not limited to, diphenyl-hexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc.

Other exemplary lipophilic moietites include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyi, cis-5-norbornene-endo-2,3-dicarbonyl, 5-norbornen-2-ylacetyl, (1R)-(–)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

The hedgehog polypeptide can be linked to the hydrophobic moiety in a number of ways including by chemical coupling means, or by genetic engineering.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, the hedgehog therapeutic is a polypeptide encodable by a nucleotide sequence that hybridizes under stringent conditions to a hedgehog coding sequence represented in one or more of SEQ ID Nos:1-7. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from MRNA or genomic DNA samples using techniques well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Preferred nucleic acids encode a hedgehog polypeptide comprising an amino acid sequence at least 60% homologous or identical, more preferably 70% homologous or identical, and most preferably 80% homologous or identical with an amino acid sequence selected from the group consisting of SEQ ID Nos:8-14. Nucleic acids which encode polypeptides at least about 90%, more preferably at least about 95%, and most preferably at least about 98-99% homology or identity with an amino acid sequence represented in one of SEQ ID Nos:8-14 are also within the scope of the invention.

In addition to native hedgehog proteins, hedgehog polypeptides preferred by the present invention are at least 60% homologous or identical, more preferably 70% homologous or identical and most preferably 80% homologous or identical with an amino acid sequence represented by any of SEQ ID Nos:8-14. Polypeptides which are at least 90%, more preferably at least 95%, and most preferably at least about 98-99% homologous or identical with a sequence selected from the group consisting of SEQ ID Nos:8-14 are also within the scope of the invention. The only prerequisite is that the hedgehog polypeptide is capable of modulating the growth of lung cells.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques or by chemical synthesis. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID Nos:1-7.

The preferred mammalian expression vectors contain both prokaryotic sequences, to facilitate the propagation of the vector in bacteria, and one or more eukaryotic transcription units that are expressed in eukaryotic cells. The pcDNAI/ amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells.

Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a *baculovirus* expression system. Examples of such *baculovirus* expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751-757) and *Salmonella typhimurium* and its in vitro activity has been demonstrated on recombinant proteins (Miller et al. (1987) *PNAS* 84:2718-1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g.of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30-3; and Kornblihtt et al. (1985) *EMBO* 4:1755-9) can be added to the hedgehog polypeptide to support attachment of the chimeric molecule to a cell through binding ECM components (Ruoslahti et al. (1987) *Science* 238:491-497; Pierschbacheret al. (1987) *J Biol. Chem.* 262:17294-8.; Hynes (1987) *Cell* 48:549-54; and Hynes (1992) *Cell* 69:11-25).

In a preferred embodiment, the hedgehog polypeptide is isolated from, or is otherwise substantially free of, other cellular proteins, especially other extracellular or cell surface associated proteins which may normally be associated with the hedgehog polypeptide, unless provided in the form of fusion protein with the hedgehog polypeptide. The term "substantially free of other cellular or extracellular proteins" (also referred to herein as "contaminating proteins") or "substantially pure preparations" or "purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos:10-18 or 20, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioctive fragments of hedgehog polypeptide. preferred hedgehog therapeutics include at least 50 (contiguous) amino acid residues of a hedgehog polypeptide, more preferably at least 100 (contiguous), and even more preferably at least 150 (contiguous) residues.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24-197 of SEQ ID No. 15, 28-202 of SEQ ID No. 16, and 23-198 of SEQ ID No. 17. By "corresponding approximately" it is meant that the sequence of interest is at most 20 amino acid residues different in length to the reference sequence, though more preferably at most 5, 10 or 15 amino acid different in length.

As described above for recombinant polypeptides, isolated hedgehog polypeptides can include all or a portion of the amino acid sequences represented in SEQ ID No:8, SEQ ID No:9, SEQ ID No:10, SEQ ID No:11, SEQ ID No:12, SEQ ID No:13 or SEQ ID No:14, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

Still other preferred hedgehog polypeptides includes an amino acid sequence represented by the formula A-B wherein: (i) A represents all or the portion of the amino acid sequence designated by residues 1-168 of SEQ ID No:21; and B represents at least one amino acid residue of the amino acid sequence designated by residues 169-221 of SEQ ID No:21; (ii) A represents all or the portion of the amino acid sequence designated by residues 24-193 of SEQ ID No:15; and B represents at least one amino acid residue of the amino acid sequence designated by residues 194-250 of SEQ ID No:15; (iii) A represents all or the portion of the amino acid sequence designated by residues 25-193 of SEQ ID No:13; and B represents at least one amino acid residue of the amino acid sequence designated by residues 194-250 of SEQ ID No:13; (iv) A represents all or the portion of the amino acid sequence designated by residues 23-193 of SEQ ID No:11; and B represents at least one amino acid residue of the amino acid sequence designated by residues 194-250 of SEQ ID No:11; (v) A represents all or the portion of the amino acid sequence designated by residues 28-197 of SEQ ID No:12; and B represents at least one amino acid residue of the amino acid sequence designated by residues 198-250 of SEQ ID No:12; (vi) A represents all or the portion of the amino acid sequence designated by residues 29-197 of SEQ ID No:16; and B represents at least one amino acid residue of the amino acid sequence designated by residues 198-250 of SEQ ID No:16; or (vii) A represents all or the portion of the amino acid sequence designated by residues 23-193 of SEQ ID No. 17, and B represents at least one amino acid residue of the amino acid sequence designated by residues 194-250 of SEQ ID No. 17. In certain preferred embodiments, A and B together represent a contiguous polypeptide sequence designated sequence, A represents at least 25, 50, 75, 100, 125 or 150 (contiguous) amino acids of the designated sequence, and B represents at least 5, 10, or 20 (contiguous) amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above. In preferred embodiments, the hedgehog polypeptide includes a C-terminal glycine (or other appropriate residue) which is derivatized with a cholesterol.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein. For example, Román et al. (1994) *Eur J Biochem* 222:65-73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack N-glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that one could reasonably expect that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine, (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W H Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as either agonists or antagonist. To illustrate, hedgehog homologs can be engineered by the present method to provide more efficient binding to a cognate receptor, such as patched, yet still retain at least a portion of an activity associated with hedgehog. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al state at page 1239 "[s]screening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO 92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8:309-314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

which would be conservative substitutions for the amino acids which appear naturally in each of those positions. For instance, Xaa(1) represents Gly, Ala, Val, Leu, Ile, Phe, Tyr or Trp ; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gin; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gin, Asn, Glu, or Asp; Xaa(14) represents His, Phe, Tyr, Thr, Gin, Asn, Glu or Asp; Xaa(15) represents Gin, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gin, Ser, Thr or Cys; Xaa(18) represents Arg, Lys, Met or Ile; Xaa(19) represents Ala, Gly, Cys, Asp, Glu, Gin, Asn, Ser, Thr or Met; Xaa(20) represents Ala, Gly, Cys, Asp, Asn, Glu or Gin; Xaa(21) represents Arg, Lys, Met, Ile, Asn, Asp, Glu or Gin; Xaa(22) represent Leu, Val, Met or Ile; Xaa(23) represents Phe, Tyr, Thr, His or Trp; Xaa(24) represents Ile, Val, Leu or Met; .Xaa(25) represents Met, Cys, Ile, Leu, Val, Thr or Ser; Xaa(26) represents Leu, Val, Met, Thr or Ser. In an even more expansive library, each X can be selected from any amino acid.

```
C-G-P-G-R-G-X(1)-G-X(2)-R-R-H-P-K-K-L-T-P-L-A-Y-K-Q-F-I-P-N-V-A-    (SEQ ID No: 21)

E-K-T-L-G-A-S-G-R-Y-E-G-K-I-X(3)-R-N-S-E-R-F-K-E-L-T-P-N-Y-N-P-

D-I-I-F-K-D-E-E-N-T-G-A-D-R-L-M-T-Q-R-C-K-D-K-L-N-X(4)-L-A-I-S-

V-M-N-X(5)-W-P-G-V-X(6)-L-R-V-T-E-G-W-D-E-D-G-H-H-X(7)-E-E-S-L-

H-Y-E-G-R-A-V-D-I-T-T-S-D-R-D-X(8)-S-K-Y-G-X(9)-L-X(10)-R-L-A-V-

E-A-G-F-D-W-V-Y-Y-E-S-K-A-H-I-H-C-S-V-K-A-E-N-S-V-A-A-K-S-G-G-C-

F-P-G-S-A-X(11)-V-X(12)-L-X(13)-X(14)-G-G-X(15)-K-X-(16)-V-K-D-

L-X(17)-P-G-D-X(18)-V-L-A-A-D-X(19)-X(20)-G-X(21)-L-X(22)-X(23)-

S-D-F-X(24)-X(25)-F-X(26)-D-R
``` wherein each of the degenerate positions "X" can be an amino acid which occurs in that position in one of the human, mouse, chicken or zebrafish Shh clones, or, to expand the library, each X can also be selected from amongst amino acid residue In similar fashion, alignment of each of the human, mouse, chicken and zebrafish hedgehog clones, can provide a degenerate polypeptide sequence represented by the general formula:

```
C-G-P-G-R-G-X(1)-X(2)-X(3)-R-R-X(4)-X(5)-X(6)-P-K-X(7)-L-X(8)-P-    (SEQ ID No: 22)

L-X(9)-Y-K-Q-F-X(10)-P-X(11)-X(12)-X(13)-E-X(14)-T-L-G-A-S-G-X (15)-X(16)-E-G-X(17)-X(18)-X(19)-R-X(20)-S-E-R-F-X(21)-X(22)-L-

T-P-N-Y-N-P-D-I-I-F-K-D-E-E-N-X(23)-G-A-D-R-L-M-T-X(24)-R-C-K-X (25)-X(26)-X(27)-N-X(28)-L-A-I-S-V-M-N-X(29)-W-P-G-V-X(30)-L-R-

V-T-E-G-X(31)-D-E-D-G-H-H-X(32)-X(33)-X(34)-S-L-H-Y-E-G-R-A-X (35)-D-I-T-T-S-D-R-D-X(36)-X(37)-K-Y-G-X(38)-L-X(39)-R-L-A-V-E-

A-G-F-D-W-V-Y-Y-E-S-X(40)-X(41)-H-X(42)-H-X(43)-S-V-K-X(44)-X

(45)
``` wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr; Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, SA (1983) *Tetrahedron* 39:3; Itakura et al. (1.981) *Recombinant DNA, Proc 3rd Cleveland Sympos. Macromolecules*, ed. A G Walton, Amsterdam: Elsevier pp273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with lung cells, e.g., lung mesenchymal or epithelial cells. A functional hedgehog protein secreted by the cells expressing the combinatorial library will diffuse to the neighboring lung cells and induce a particular biological response, such as proliferation. The pattern of detection of proliferation will resemble a gradient function, and will allow the isolation (generally after several repetitive rounds of selection) of cells producing hedgehog homologs active as proliferative agents with respect to the lung cells. Likewise, hedgehog antagonists can be selected in similar fashion by the ability of the cell producing a functional antagonist to protect neighboring cells (e.g., to inhibit proliferation) from the effect of wild-type hedgehog added to the culture media.

To illustrate, target lung cells are cultured in 24-well microtitre plates. Other eukaryotic cells are transfected with the combinatorial hedgehog gene library and cultured in cell culture inserts (e.g. Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as proliferation, the inserts are removed and the effect of the variant hedgehog proteins on the target cells determined. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370-1371; and Goward et al. (1992) *TIBS* 18:136-140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E.coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007-16010; Griffths et al. (1993) EMBO J 12:725-734; Clackson et al. (1991) Nature 352:624-628; and Barbas et al. (1992) PNAS 89:4457-4461).

In an illustrative embodiment, the recombinant phage antibody system (RPAS, Pharamacia Catalog number 27-9400-01) can be easily modified for use in expressing and screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811-7815; Yourvan et al., 1992, *Parallel Problem Solving from Nature,* 2., In Maenner and Manderick, eds., Elsevir Publishing Co., Amsterdam, pp. 401-410; Delgrave et al., 1993, *Protein Engineering* 6(3):327-33 1).

The invention also provides for reduction of the hedgehog protein to generate mimetics, e.g. peptide or non-peptide agents, which are able to disrupt binding of a hedgehog polypeptide of the present invention with an hedgehog receptor. Thus, such mutagenic techniques as described above are also useful to map the determinants of the hedgehog proteins which participate in protein-protein interactions involved in, for example, binding of the subject hedgehog polypeptide to other extracellular matrix components. To illustrate, the critical residues of a subject hedgehog polypeptide which are involved in molecular recognition of an hedgehog receptor such as patched can be determined and used to generate hedgehog-derived peptidomimetics which competitively inhibit binding of the authentic hedgehog protein with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. Such mimetics may then be used to interfere with the normal function of a hedgehog protein. For instance, non-hydrolyzable peptide analogs of such residues can be generated using benzodiazepine (e.g., see Freidinger et al. in *Peptides. Chemistry and Biology,* G. R. Marshall ed., ESCOM Publisher: Leiden, Netherlands, 1988), azepine (e.g., see Huffman et al. in *Peptides: Chemistry and Biology,* G. R. Marshall ed., ESCOM Publisher: Leiden, Netherlands, 1988), substituted gama lactam rings (Garvey et al. in *Peptides: Chemistry and Biology,* G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al (1985) *Biochem Biophys Res Commun* 126:419; and Dann et al. (1986) *Biochem Biophys Res Commun* 134:71).

Recombinantly produced forms of the hedgehog proteins can be produced using, e.g., expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the *baculovirus* system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either an agonistic or antagonistic form of a hedgehog polypeptide. Thus, another aspect of the invention features expression vectors for in vivo transfection of a hedgehog polypeptide in particular cell types so as cause ectopic expression of a hedgehog polypeptide in lung tissue.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including lung cells, in vitro and/or in vivo (see for example Eglitis, et al. (1985) *Science* 230:1395-1398; Danos and Mulligan (1988) *Proc. Natl. Acad Sci.* USA 85:6460-6464; Wilson et al. (1988) *Proc. Natl. Acad Sci. USA* 85:3014-3018; Armentano et al. (1990) *Proc. Natl. Acad Sci. USA* 87:6141-6145; Huber et al. (1991) *Proc. Natl. Acad. Sci. USA* 88:8039-8043; Ferry et al. (1991) *Proc. Natl. Acad Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by. modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079-9083; Julan et al. (1992) *J. Gen Virol* 73:3251-3255; and Goud et al. (1983) *Virology* 163: 251-254); or coupling cell surface receptor ligands to the viral env proteins (Neda et al. (1991) *J Biol Chem* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Bio Techniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including lung cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J Virol* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054-3057). A hedgehog expression construct can be delivered in a gene therapy construct to dermal cells by, e.g., electroporation using techniques described, for example, by Dev et al. ((1994) *Cancer Treat Rev* 20:105-115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the ptc, hedgehog or fgf-10 therapeutic can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes constitutive expression of the hedgehog gene or which causes inducible expression of the gene under conditions different from the normal expression pattern of the gene. Other genes in the patched signaling pathway can be similarly targeted. A variety of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.) which direct recombination and (2) heterologous transcriptional regulatory sequence(s) which is to be operably linked to the coding sequence for the genomic hedgehog gene upon recombination of the gene activation construct. For use in generating cultures of hedgehog producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, *J Exp. Med,* 169:13), the human β-actin promoter (Gunning et al. (1987) *PNAS* 84:4831-4835), the glucocorticoid-inducible promoter present in the mouse mammary tumor virus long terminal repeat (MMTV LTR) (Klessig et al. (1984) *Mol. Cell Biol* 4:1354-1362), the long terminal repeat sequences of *Moloney murine* leukemia virus (MuLV LTR) (Weiss et al. (1985) *RNA Tumor Viruses*, Cold Spring Harbor Laboratory, Cold Spring Harbor, N.Y.), the SV40 early or late region promoter (Bernoist et al. (1981) *Nature* 290:304-310; Templeton et al. (1984) *Mol. Cell Biol.*, 4:817; and Sprague et al. (1983) *J. Virol.*, 45:773), the promoter contained in the 3' long terminal repeat of *Rous sarcoma* virus (RSV) (Yamamoto et al., 1980, *Cell*, 22:787-797), the herpes simplex virus (HSV) thymidine kinase promoter/enhancer (Wagner et al. (1981) *PNAS* 82:3567-71), and the herpes simplex virus LAT promoter (Wolfe et al. (1992) *Nature Genetics,* 1:379-384).

In an exemplary embodiment, portions of the 5' flanking region of the human Shh gene are amplified using primers which add restriction sites, to generate the following fragments (SEQ ID NOS. 25 AND 26, respectively)

```
5'-gcgcgcttcgaaGCGAGGCAGCCAGCGAGGGAGAGAGCGAGCGGGCGAGCCGGAGC-
GAGGAAatcgatgcgcgc (primer 1)

5'-gcgcgcagatctGGGAAAGCGCAAGAGAGAGCGCACACGCACACACCCGCCGCGCG-
CACTCGggatccgcgcgc (primer 2)
```

As illustrated, primer 1 includes a 5' non-coding region of the human Shh gene and is flanked by an AsuII and ClaI restriction sites. Primer 2 includes a portion of the 5' non-coding region immediately 3' to that present in primer 1. The hedgehog gene sequence is flanked by XhoII and BamHI restriction sites. The purified amplimers are cut with each of the enzymes as appropriate.

The vector pCDNA1.1 (Invitrogen) includes a CMV promoter. The plasmid is cut with -with AsuII, which cleaves just 3' to the CMV promoter sequence. The AsuII/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, an cut with AsuII and BamHI to produce the gene activation construct (SEQ ID NO: 27)

In still other embodiments, the replacement region merely deletes a negative transcriptional control element of the native gene, e.g., to activate expression, or ablates a positive control element, e.g., to inhibit expression of the targeted gene.

V. Exemplary ptc Therapeutic Compounds.

In another embodiment, the subject method is carried out using a ptc therapeutic composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly their role in the pathogenesis of proliferation and/or differentiation of various lung cells and maintenance of lung tissue. In one embodiment, the assay evaluates the

```
cgaagcgaggcagccagcgagggagagagcgagcgggcgagccggagcgaggaaATCGAAGG

TTCGAATCCTTCCCCCACCACCATCACTTTCAAAAGTCCGAAAGAATCTGCTCCCTGCTTGT

GTGTTGGAGGTCGCTGAGTAGTGCGCGAGTAAAATTTAAGCTACAACAAGGCAAGGCTTGAC

CGACAATTGCATGAAGAATCTGCTTAGGGTTAGGCGTTTTGCGCTGCTTCGCGATGTACGGG

CCAGATATACGCGTTGACATTGATTATTGACTAGTTATTAATAGTAATCAATTACGGGGTCA

TTAGTTCATAGCCCATATATGGAGTTCCGCGTTACATAACTTACGGTAAATGGCCCGCCTGG

CTGACCGCCCAACGACCCCCGCCCATTGACGTCAATAATGACGTATGTTCCCATAGTAACGC

CAATAGGGACTTTCCATTGACGTCAATGGGTGGACTATTTACGGTAAACTGCCCACTTGGCA

GTACATCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACATCTACG

TATTAGTCATCGCTATTACCATGGTGATGCGGTTTTGGCAGTACATCAATGGGCGTGGATAG

CGGTTTGACTCACGGGGATTTCCAAGTCTCCACCCCATTGACGTCAATGGGAGTTTGTTTTG

GCACCAAAATCAACGGGACTTTCCAAAATGTCGTAACAACTCCGCCCCATTGACGCAAATGG

GCGGTAGGCGTGTACGGTGGGAGGTCTATATAAGCAGAGCTCTCTGGCTAACTAGAGAACCC

ACTGCTTACTGGCTTATCGAAATTAATACGACTCACTATAGGGAGACCCAAGCTTGGTACCG

AGCTCGGATCgatctgggaaagcgcaagagagagcgcacacgcacacacccgccgcgcgcac tcgg
```

In this construct, the flanking primer 1 and primer 2 sequences provide the recombination region which permits the insertion of the CMV promoter in front of the coding sequence for the human Shh gene. Other heterologous promoters (or other transcriptional regulatory sequences) can be inserted in a genomic hedgehog gene by a similar method.

ability of a compound to modulate binding between a hedgehog polypeptide and a hedgehog receptor such as patched. In other embodiments, the assay merely scores for the ability of a test compound to alter the signal transduction acidity of the patched protein. In this manner, a variety of hedgehog and/or ptc therapeutics, both proliferative and anti-proliferative in activity, can be identified. A variety of assay formats will suffice and, in light of the present disclosure, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Accordingly, in an exemplary screening assay for ptc therapeutics, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. The efficacy of the compound can be assessed by generating dose response curves from data obtained using various concentrations of the test compound. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

In other embodiments, a ptc therapeutic of the present invention is one which disrupts the association of patched with smoothened.

Agonist and antagonists of cell growth can be distinguished, and the efficacy of the compound can be assessed, by subsequent testing with certain lung cells, e.g., in culture.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see GenBank Accession numbers U40074 for chicken patched and U46155 for mouse patched), as well as from drosophila (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g. corresponding to residues Asn120-Ser438 and/or Arg770-Trp1027 of the human patched protein—which are also potential antagonists of hedgehog-dependent signal transduction). For instance, the patched protein can be provided in soluble form, as for example a preparation of one of the extracellular domains, or a preparation of both of the extracellular domains which are covalently connected by an unstructured linker (see, for example, Huston et al. (1988) PNAS 85:4879; and U.S. Pat. No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cell by standard recombinant DNA techniques. These recombinant cells can be used for receptor binding, signal transduction or gene expression assays. Marigo et al. (1996) Development 122:1225-1233 illustrates a binding assay of human hedgehog to chick patched protein ectopically expressed in Xenopus laevis oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150-21157) which includes a 10-residue sequence from c-myc, as well as the pFLAG system (International Biotechnologies, Inc.) or the pEZZ-protein A system (Pharamacia, N.J.).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68:809-818; Newton et al. (1983) *Biochemistry* 22:6110-6117; and Reber et al. (1987) *J. Biol Chem* 262:11369-11374).

In addition to cell-free assays, such as described above, the readily available source of hedgehog proteins provided by the art also facilitates the generation of cell-based assays for identifying small molecule agonists/antagonists and the like. Analogous to the cell-based assays described above for screening combinatorial libraries, cells which are sensitive to hedgehog induction, e.g. patched-expressing cells or other lung-derived cells sensitive to hedgehog induction, can be contacted with a hedgehog protein and a test agent of interest, with the assay scoring for anything from simple binding to the cell to modulation in hedgehog inductive responses by the target cell in the presence and absence of the test agent. As with the cell-free assays, agents which produce a statistically significant change in hedgehog activities (either inhibition or potentiation) can be identified.

In other embodiments, the cell-based assay scores for agents which disrupt association of patched and smoothened proteins, e.g., in the cell surface membrane or liposomal preparation.

In addition to characterizing cells that naturally express the patched protein, cells which have been genetically engineered to ectopically express patched can be utilized for drug screening assays. As an example, cells which either express low levels or lack expression of the patched protein, e.g. *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or antagonists of hedgehog binding. Binding assays can be performed using whole cells. Furthermore, the recombinant cells of the present invention can be engineered to include other heterologous genes encoding proteins involved in hedgehog-dependent signal pathways. For example, the gene products of one or more of smoothened, costal-2 and/or fused can be co-expressed with patched in the reagent cell, with assays being sensitive to the functional reconstitution of the hedgehog signal transduction cascade.

Alternatively, liposomal preparations using reconstituted patched protein can be utilized. Patched protein purified from detergent extracts from both authentic and recombinant origins can be reconstituted in artificial lipid vesicles (e.g. phosphatidylcholine liposomes) or in cell membrane-derived vesicles (see, for example, Bear et al. (1992) *Cell* 68:809-818; Newton et al. (1983) *Biochemistry* 22:6110-6117; and Reber et al. (1987) *J Biol Chem* 262:11369-11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists or antagonists, of hedgehog or patched activities. By detecting changes in intracellular signals, such as alterations in second messengers or gene expression, in patched-expressing cells contacted with a test agent, candidate agonists and antagonists to patched signaling can be identified.

A number of gene products have been implicated in patched-mediated signal transduction, including patched, the transcription factor cubitus interruptus (ci), the serine/threonine kinase fused (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 *Development* 110, 291-301; Marigo et al., 1996) and the vertebrate homologs of the *drosophila* cubitus interruptus gene, the GLI genes (Hui et al. (1994) *Dev Biol* 162:402-413). Patched gene expression has been shown to be induced in cells of the limb bud and the neural plate that are responsive to Shh. (Marigo et al. (1996) *PNAS;* Marigo et al. (1996) *Development* 122:1225-1233). The GLI genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the GLI gene has been reported to be upregulated in response to hedgehog in limb buds, while transcription of the GLI3 gene is downregulated in response to hedgehog induction (Marigo et al. (1996) *Development* 122:1225-1233). By selecting transcriptional regulatory sequences from such target genes, e.g. from patched or GLI genes, that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as agonists or antagonists of ptc induction of differentiation/quiescence.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270:10314-10322; and Kube et al. (1995) *Cytokine* 7:1-7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsive to patched-dependent signaling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (dewet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) Genes & Dev 10:647). High PKA activity has been shown to antagonize hedgehog signaling in these systems. Although it is unclear whether PKA acts directly downstream or in parallel with hedgehog signaling, it is possible that hedgehog signalling occurs via inhibition of PKA activity. Thus, detection of PKA activity provides a potential readout for the instant assays.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

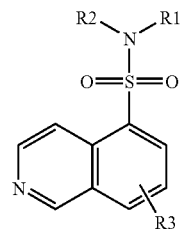

wherein,

R₁ and R₂ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH₂)ₘ—R₈, —(CH₂)ₘ—OH, —(CH₂)ₘ—O-lower alkyl, —(CH₂)ₘ—O—lower alkenyl, —(CH₂)ₙ—O—(CH₂)ₘ—R₈, —(CH₂)ₘ—SH, —(CH₂)ₘ—S-lower alkyl, —(CH₂)ₘ—S-lower alkenyl, —(CH₂)ₙ—S—(CH₂)ₘ—R₈, or R₁ and R₂ taken together with N form a heterocycle (substituted or unsubstituted);

R₃ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH₂)ₘ—R₈, —(CH₂)ₘ—OH, —(CH₂)ₘ—O-lower alkyl, —(CH₂)ₘ—O-lower alkenyl, —(CH₂)ₙ—O—(CH₂)ₘ—R₈, —(CH₂)ₘ—SH, —(CH₂)ₘ—S-lower alkyl, —(CH₂)ₘ—S-lower alkenyl, —(CH₂)ₙ—S—(CH₂)ₘ—R₈;

R₈ represents a substituted or unsubstituted aryl, aralkyl, cycloalkyl, cycloalkenyl, or heterocycle; and n and m are independently for each occurrence zero or an integer in the range of 1 to 6.

In a preferred embodiment, the PKA inhibitor is N-[2-((p-bromocinnamyl)amino)ethyl]-5-isoquinolinesulfonamide (H-89; Calbiochem Cat. No. 371963), e.g., having the formula:

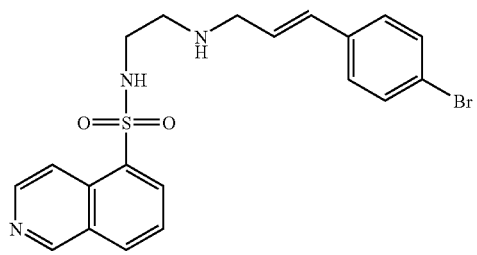

In another embodiment, the PKA inhibitor is 1-(5-isoquinolinesulfonyl)-2-methylpiperazine (H-7; Calbiochem Cat. No. 371955), e.g., having the formula:

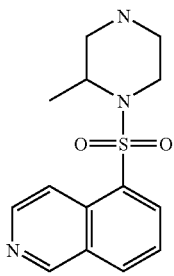

In still other embodiments, the PKA inhibitor is KT5720 (Calbiochem Cat. No. 420315), having the structure

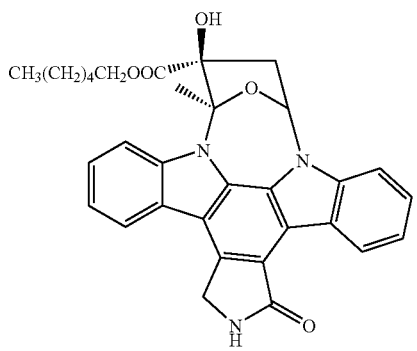

A variety of nucleoside analogs are also useful as PKA inhibitors. For example, the subject method can be carried out cyclic AMP analogs which inhibit the kinase activity of PKA, as for example, 8-bromo-cAMP or dibutyryl-cAMP

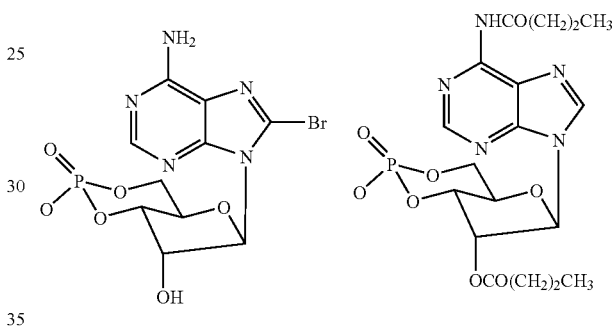

Exemplary peptidyl inhibitors of PKA activity include the PKA Heat Stable Inhibitor (isoform α; see, for example, Calbiochem Cat. No. 539488, and Wen et al. (1995) *J Biol Chem* 270:2041).

Certain hedgehog receptors may stimulate the activity of phospholipases. Inositol lipids can be extracted and analyzed using standard lipid extraction techniques. Water soluble derivatives of all three inositol lipids ($IP_1$, $P_2$. $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45-56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the *drosophila* gene fused (fu) which encodes a serine/threonine kinase has been identified as a potential downstream target in hedgehog signaling. (Preat et al., 1990 *Nature* 347, 87-89; Therond et al. 1993, *Mech. Dev.* 44. 65-80). The ability of compounds to modulate serine/threonine kinase activation could be screened using colony immunoblotting (Lyons and Nelson (1984) *Proc. Natl. Acad Sci. USA* 81:7426-7430) using antibodies against phosphorylated serine or threonine residues. Reagents for performing such assays are commercially available, for example, phosphoserine and phosphothreonine specific antibodies which measure increases in phosphorylation of those residues can be purchased from comercial sources.

In yet another embodiment, the ptc therapeutic is an antisense molecule which inhibits expression of a protein involved in a patched-mediated signal transduction pathway. To illustrate, by inhibiting the expression of a protein which are involved in patched signals, such as fused, costal-2, smoothened and/or Gli genes, the ability of the patched signal pathway(s) to inhibit proliferation of a cell can be altered, e.g., potentiated or repressed.

As used herein, "antisense" therapy refers to administration or in situ generation of oligonucleotide probes or their derivatives which specifically hybridize (e.g. bind) under cellular conditions with cellular mRNA and/or genomic DNA encoding a hedgehog protein, patched, or a protein involved in patched-mediated signal transduction. The hybridization should inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958-976; and Stein et al. (1988) *Cancer Res* 48:2659-2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25-26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc therapeutic can be an antisense construct for inhibiting the expression of patched, e.g., to mimic the inhibition of patched by hedgehog. Exemplary antisense constructs include: (SEQ ID NOS. 28, 29 and 30, respectively, in order of appearance)

```
5'-GTCCTGGCGCCGCCGCCGCCGTCGCC

5'-TTCCGATGACCGGCCTTTCGCGGTGA

5'-GTGCACGGAAAGGTGCAGGCCACACT
```

VI. Exemplary Pharmaceutical Preparations of Hedgehog and ptc Therapeutics

The source of the hedgehog and ptc therapeutics to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, inter alia, from PCT publications WO 95/18856 and WO 96/17924.

Those of skill in treating lung tissues can determine the effective amount of an ptc, hedgehog or fgf-10 therapeutic to be formulated in a pharmaceutical or cosmetic preparation.

The ptc, hedgehog or fgf-10 therapeutic formulations used in the method of the invention are most preferably applied in the form of appropriate compositions. As appropriate compositions there may be cited all compositions usually employed for systemically or topically administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular ptc, hedgehog or fgf-10 therapeutic as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

As appropriate compositions for topical application there may be cited all compositions usually employed for topically administering therapeutics, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the subject compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications which can be considered cosmetic uses. Cosmetic compositions known in the art, preferably hypoallergic and pH controlled are especially preferred, and include toilet waters, packs, lotions, skin milks or milky lotions. The preparations contain, besides the ptc, hedgehog or fgf-10 therapeutic, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the ptc, hedgehog or fgf-10 therapeutic, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2-15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10-50% of oil, 1 to 10% of surfactant, 50-80% of water and 0 to 3% of preservative and/or perfume. In the aforementioned preparations, all % symbols refer to weight by weight percentage.

Particular compositions for use in the method of the present invention are those wherein the ptc, hedgehog or fgf-10 therapeutic is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of ptc, hedgehog or fgf-10 therapeutic, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc therapeutics is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated ptc, hedgehog or fgf-10 therapeutic can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which. can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanol-amine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Apart from the above-described compositions, use may be made of covers, e.g. plasters, bandages, dressings, gauze pads and the like, containing an appropriate amount of a ptc, hedgehog or fgf-10 therapeutic. In some cases use may be made of plasters, bandages, dressings, gauze pads and the like which have been impregnated with a topical formulation containing the therapeutic formulation.

EXEMPLIFICATION

The invention now being generally described, it will be more readily understood by reference to the following examples which are included merely for purposes of illustration of certain aspects and embodiments of the present invention, and are not intended to limit the invention.

The mammalian lung, like many other organs, develops by branching morphogenesis of an epithelium [see ref. 1]. Development initiates with evagination of two ventral buds of foregut endoderm into the underlying splanchnic mesoderm. As they extend, they send out lateral branches at precise, invariant positions establishing the primary airways and the lobes of each lung. Dichotomous branching leads to further extension of the airways. Grafting studies have demonstrated the importance of bronchial mesenchyme in inducing epithelial branching, but the significance of epithelial signaling is largely unstudied. The morphogen Sonic hedgehog (Shh) is widely expressed in the foregut endoderm and is specifically up-regulated in the distal epithelium of the lung where branching is occurring [see ref. 2]. Ectopic expression of Shh disrupts branching and increases proliferation suggesting that local Shh signaling regulates lung development [see ref. 2]. We report here that Shh is essential for development of the respiratory system. In Shh null mutants, the trachea and esophagus do not separate properly and the lungs form a rudimentary sac due to failure of branching and growth after formation of the primary lung buds. Interestingly, normal proximo-distal differentiation of the airway epithelium occurs, indicating that Shh is not needed for differentiation events. In addition, the transcription of several mesenchymally expressed downstream targets of Shh is abolished. These results highlight the importance of epithelially derived Shh in regulating branching morphogenesis of the lung.

Results and Discussion

Figure 1B:
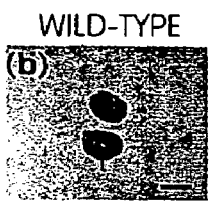
Figure 1E:
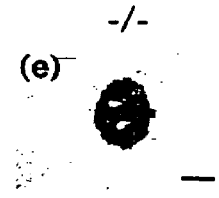
Figure 1C:
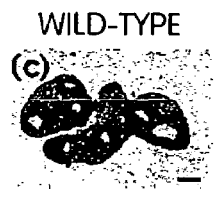
Figure 1F:
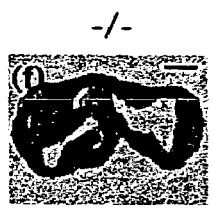

To address the role of Shh in respiratory tract development, we examined a null mutant of the gene (3). At 10.5 days post coitum (dpc) of embryonic mouse development, the lung of wild-type (wt) siblings consists of a left and right bud [see ref. 1]. By 12.5 dpc, the trachea epithelium has separated ventrally from the esophageal component of the foregut and the two lung buds have formed several lateral branches which will give rise to primary airways of the lung lobes (FIGS. 1*a-c*). In contrast, the esophageal and tracheal tubes remain closely associated in Shh mutants (FIGS. 1*d,e*) and although left and right buds form, they either have not branched or possess one abnormally positioned branch point (FIG. 1*f*). Wild-type lungs undergo considerable growth and branching in organ culture. However, in explant culture of lungs from Shh mutants, bronchial mesenchyme cells detach from the endoderm and the epithelium fails to grow, or branch extensively (data not shown). We conclude that the defect in branching morphogenesis is independent of other Shh-expressing organs (i.e., the gut), and that the observed branching phenotype reflects an absence of Shh signaling which is normally associated with the branching process.

Figure 1G:
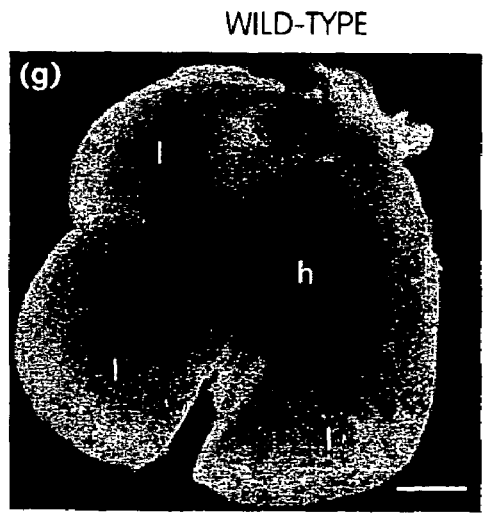
Figure 1H:
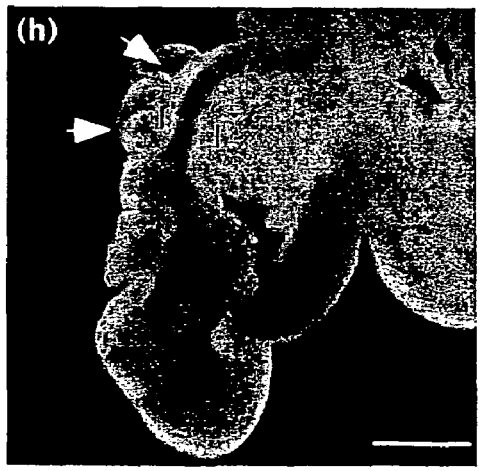
Figure 1I:
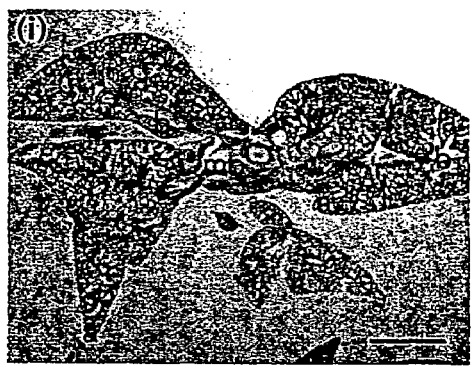
Figure 1J:
Figure 1K:
Figure 1M:
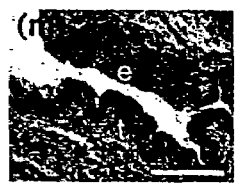
Figure 1L:
Figure 1N:
Figure 1O:

To determine if branching is merely delayed and whether Shh plays a role in differentiation, we examined lungs removed at 15.5 (data not shown) and 18.5 dpc (FIGS. 1*g,h*). At this time, five well-developed lobes are evident in the wild-type (four right, one left), and highly branched airways form a ramifying epithelial network, the respiratory tree (FIGS. 1*i,k,l*). To mediate gas exchange in the alveolar sacs, the respiratory surface is well vascularized (FIG. 1*g*). In contrast, Shh mutants form only a rudimentary respiratory organ with a few large, poorly vascularized airways (FIG. 1*h*). Trachea and esophagus are so closely juxtaposed that their tubes share some common epithelium (FIG. 1e) and a fistula-like fusion of the alimentary and respiratory tract is formed, mirroring a lethal anomaly well described in human pathology [see ref. 4,5] (FIGS. 1j,m).

Figure 1Q:
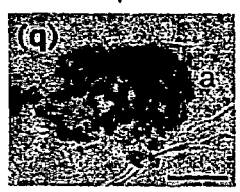
Figure 1P:
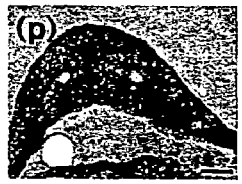
Figure 1R:
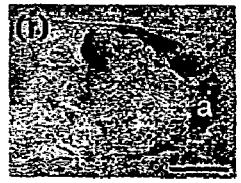

Remarkably, despite the absence of branching, evidence of normal proximo-distal epithelial differentiation can be observed. Most proximally, the pulmonary epithelium forms a columnar epithelium typical of the mainstem bronchi (FIG. 1m) and expresses CCSP [see ref. 6], a marker for terminally differentiated secretory Clara cells (FIG. 1q). More distally, the epithelium consists of a mixture of columnar and cuboidal epithelium as observed in the bronchioles (FIG. 1n), and alveolar air sacs are formed which correspondingly express SP-C [see ref. 7], a type II pneumocyte marker (FIG. 1r).

In summary, Shh is not required for proximo-distal differentiation of lung epithelium, but is essential for three different events of regional morphogenesis of the foregut endoderm, formation of the tracheoesophageal septum, lung lobation and generation of the respiratory tree, all of which are essential in forming a functional lung.

The exact role for Shh in branching processes remains to be determined. Grafting studies indicate that, whereas budding can be supported by mesenchyme from many different sources, only bronchial mesenchyme can induce organotypic branching morphogenesis [see ref. 8]. The requirement for Shh in the epithelium suggests that regulation of its expression may be a reciprocal epithelial response to mesenchymal signaling.

To examine in more detail how Shh might regulate early branching of the lung epithelium, we performed digoxigenin in situ hybridization with probes recognizing general targets of Hedgehog signaling (FIGS. 2a-e and data not shown), or genes specifically implicated in lung morphogenesis (FIGS. 2f-k). As Shh mutants are growth retarded and show a general delay in lung budding, we compared expression of these markers at 12.5 dpc with wild type embryos collected at 11.5 and 12.5 dpc.

Figure 2A:
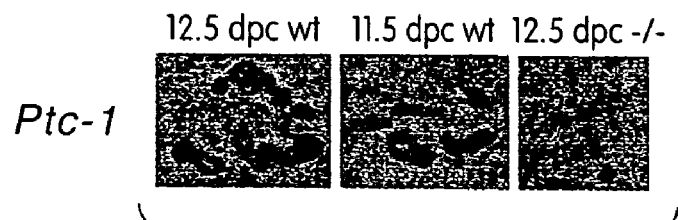
Figure 2B:
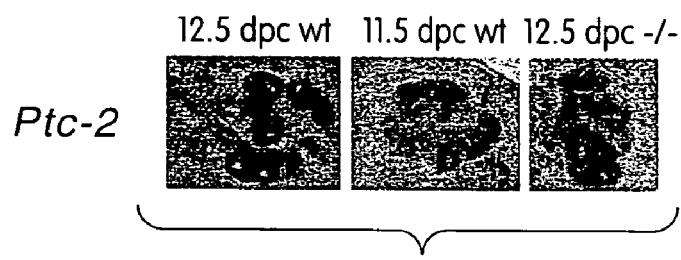
Figure 2C:
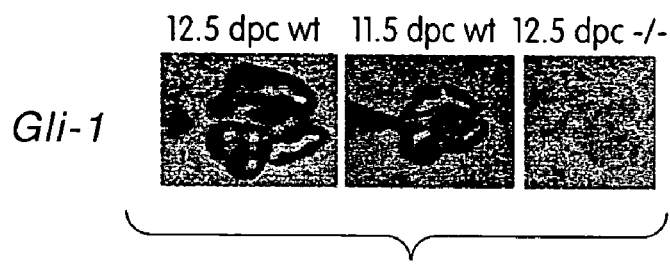
Figure 2D:
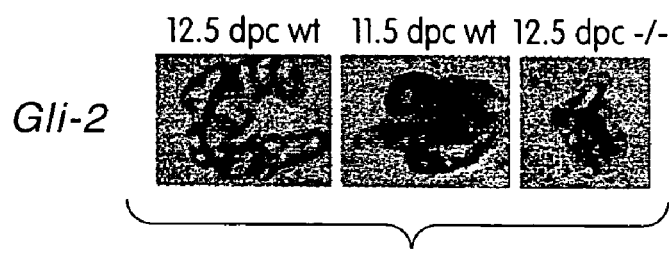
Figure 2E:
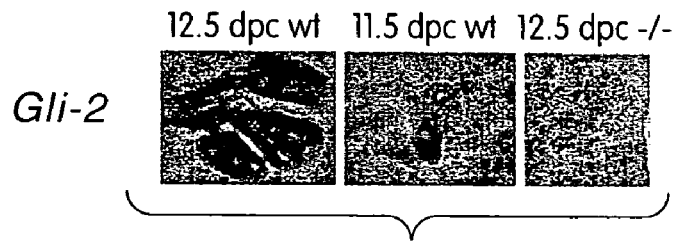
Figure 2F:
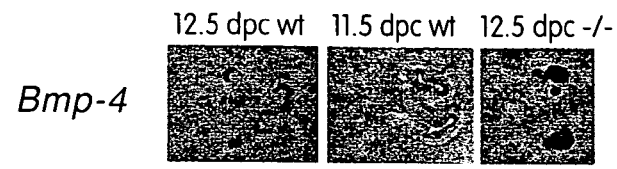
Figure 2G:
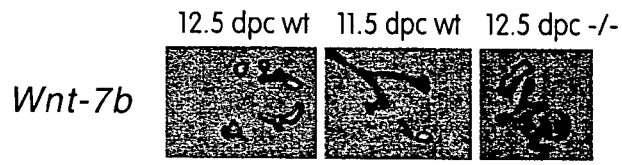

Patched genes encode proteins thought to be Hedgehog receptors, while Gli-genes encode transcriptional mediators of Hedgehog signaling [see ref. 9]. Both Ptc-1 and Gli-1 are up-regulated when Shh is ectopically expressed in the lung indicating that here, as elsewhere in the embryo, they are transcriptional targets of Shh signaling [see ref. 9,10]. Consistent with this model, Ptc-1 and Gli-1 are normally expressed in the mesenchyme of wild-type embryos with highest levels at the distal branch points mirroring epithelial Shh expression [see ref. 10] (FIGS. 2a,c). In Shh mutants, only basal levels of expression of both genes are detected (FIGS. 2a,c). Gli-3 which shows more wide-spread expression in the mesenchyme is also down-regulated (FIG. 2e). In contrast, Ptc-2 which is expressed at higher levels in the epithelium and Gli-2, which is normally expressed more uniformly in the mesenchyme are not altered (FIG. 2b,d). These data indicate that the lung mesenchyme, not the epithelium, is most likely the direct cellular target of Shh signaling. Further, they suggest that modulation of Gli-1 and Gli-3 transcription may be a critical aspect of lung morphogenesis. As Gli-1 mutants do not have a lung phenotype, the Shh phenotype cannot simply be ascribed to a loss of Gli-1 transcriptional activity [see ref. 10]. Given that post-transcriptional processing regulates Gli (Ci) activity in invertebrates [see ref. 11], we cannot rule out that Gli-2 is expressed, but posttranscriptionally inactivated. Gli genes are clearly involved in lung development, as evidenced by the relatively weak lobular hypoplasia observed in Gli-3 mutants [see ref. 10], but revealing the full extent of Gli action may require the generation of compound mutants.

Figure 2H:

Several lines of evidence indicate that hedgehog signaling regulates the expression of Bmp, Wnt and FGF family members [see ref. 11]. In the lung, Bmp-4 is strongly expressed in the distal-most tips of the epithelium. Ectopic expression results in decreased epithelial proliferation, disrupted branching and reduced differentiation of distal cell types in the airway [see ref. 12]. In Shh mutants, Bmp 4 is expressed in the normal position but at higher levels (FIG. 2f), suggesting that enhanced Bmp 4 signaling could contribute to the block in branching. Wnt-7b is normally expressed in the lung epithelium and is required for normal branching (S. Lee, W. Cardoso, B. Parr & A. McMahon; unpublished), whereas Wnt-2 is expressed in the underlying mesenchyme suggesting a role in epithelial maintenance [see ref. 2]. In Shh mutants, Wnt-7b expression is not altered (FIG. 2g) but Wnt-2 expression is down-regulated (FIG. 2h). This observation lends further support to the model that the lung mesenchyme is the primary target of Shh signaling and indicates that mesenchymal signaling is abnormal in Shh mutants. However, no role for Wnt-2 in lung development has been reported in Wnt-2 mutants [see ref. 13].

Figure 2I:
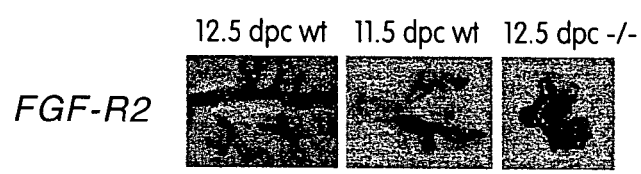
Figure 2J:

Ectopic expression of a dominant negative form of FGF-R2 in the lung epithelium arrests branching after formation of left and right buds which then grow caudally as tubes, differentiating into proximal epithelial structures only [see ref. 14]. An arrest in branching after initial budding is reminiscent of Shh mutants, but there are clearly differences in subsequent morphogenesis and differentiation which is largely unaffected in Shh mutants. The recent observation that FGf10 is expressed in mesenchyme cells preceding branch formation and can induce branching of lung epithelium in culture, points to its role as a putative ligand [see ref. 15]. In Shh mutants, expression of FGF-R2 is unaltered (FIG. 2I). In contrast, Fgf10 which in wild-type embryos is highly localized to small patches of mesenchyme at a distance from the lung epithelium (arrows in FIG. 2j), is expressed broadly in mesenchyme immediately adjacent to the epithelium in the mutant lung. These results indicate that Shh is not required for Fgf10 expression. Further, they suggest that Shh signaling may spatially restrict Fgf10 expression to the distal mesenchyme. Such an inhibitory role for Shh in the local regulation of Fgf10 expression is supported by transgenic studies [see ref. 16]. The intriguing possibility that the altered position of Fgf10 expression then disrupts branching remains to be determined.

Figure 2K:

HNF-3β and Nkx-2.1 are specific transcriptional effectors of Shh signaling in the neural tube. In the gut, HNF-3b is widely expressed in the epithelium, including the lung, whereas Nkx-2.1 expression is specific to the lung epithelium and a few other endodermal derivatives [see ref. 17]. Mice lacking Nkx 2.1 deveiop cystic unbranched lungs indicating that it is essential for lung morphogenesis [see ref. 17]. Expression of both genes is unaltered in the epithelium of Shh mutant lungs suggesting that in this organ their expression is independent of the Shh signaling pathway (FIG. 2k and data not shown).

Figure 3B:

As loss of Shh activity predominantly affects the expression of mesenchyme markers, we analyzed late mesenchyme differentiation. Formation of cartilage rings, albeit disorganized, occurs in the mutant (FIG. 3a), while the layer of smooth muscle typically lining the proximal epithelium is absent (FIG. 3b). The observation that Shh is required for formation of smooth muscle is in agreement with previous studies [see ref. 18].

In summary, the results reported here establish Shh as a regulator of foregut development and more specifically as a key factor in the control of branching morphogenesis in the mouse lung. They also indicate that the genetic control of growth and branching in the lung epithelium is most likely a complex process involving both epithelial and mesenchymal interactions at the branch points, and that the downstream targets of Shh signaling in this organ are primarily mesenchymally expressed genes.

MATERIALS AND METHODS

Shh Mutants

Generation of the Shh mutants has been described elsewhere [see ref. 3]. Mice homozygous for the null allele appear phenotypically identical to those reported in [see ref. 19].

Histological/in situ Analysis

Tissue was processed for standard histology, or a modified in situ hybridization procedure [see ref. 20].

Antibody Staining

Antibody staining with a monoclonal antibody against smooth muscle actin (Sigma) was carried out according to the manufacturer's instructions.

REFERENCES CITED IN EXAMPLES

1. Ten Have-Opbroek AAW: *Lung development in the mouse embryo. Exp Lung Res* 1992, 17:111-130.
2. Bellusci S et al.: *Involvement of Sonic hedgehog (Shh) in mouse embryonic lung growth and morphogenesis. Development* 1997, 124: 53-63.
3. St.-Jacques B, Dassule H, Karavanova I, Botchkarev V A, Li J, Danielian P, McMahon J A, Paus R, Lewis P, McMahon A P: *Shh signaling is essential for hair development. Curr Biol.*, in press.
4. Sutliff K S, Hutchins G M: *Septation of the respiratory and digestive tracts in human embryos: crucial role of the tracheoesophageal sulcus. Anatom Record* 1994, 238:237-247.
5. Skandalakis J E et al: *The trachea and the lungs. Embrfor Surgeons.* 1994, 414-450.
6. Hackett B P, Gitlin J D: *Cell-specific expression of a Clara cell secretory protein-human growth hormone gene in the bronchiolar epithelium of transgenic mice. Proc Natl Acad USA* 1992, 89:9079-9083.
7. Bachurski C J, Pryhuber G S, Glasser S W, Kelly S E, Whitsett J A: *Tumor necrosis factor-alpha inhibits surfactant protein C gene transcription. J Biol Chem* 1995, 270: 19402-19407.
8. Spooner B S, Wessells N K *Mammalian lung development: interactions in primordium formation and bronchial morphogenesis. J Exp Zool* 1970, 175: 445-454.
9. Tabin C J, McMahon A P: *Recent advances in hedgehog signaling. Trends Cell Biol* 1997, 7:442-445.
10. Grindley J C, Bellusci S, Perkins D, Hogan B L M: *Evidence for the involvement of the Gli geneja mily in embryonic mouse lung development Dev Biol* 1997, 188: 337-348.
11. Hammerschmidt M, Brook A, McMahon A P: *The world according to hedgehog TIGs* 1997, 13: 14-21.
12. Bellusci S, Henderson R, Winnier G, Oikawa T, Hogan B L M: *Evidence from normal expression and targeted misexpression that Bone Morphogenetic Protein-4 (Bmp-4) plays a role in mouse embryonic lung morphogenesis. Development* 1996, 122: 1693-1702.
13. Monkley S J, et al.: *Targeted disruption of the Wnt2 gene results in placentation defects. Development* 1996, 122: 3343-3353.
14. Peters K, Werner S, Liao X, Whisett J, Williams S: *Targeted expression of a dominant negative FGF receptor blocks branching morphogenesis and epithelial differentiation of the mouse lung EMBO J* 1996, 13:3296-3301.
15. Bellusci S. et al.: *Fibroblast Growth Factor 10 and branching morphogenesis in the embryonic mouse lung. Development* 1997, 124: 4867-4878.
16. Ang S L, Rossant J: *HNF-3beta is essential for node and notochord formation in mouse development. Cell* 1994, 78:561-574.
17. Kimura S et al.: *The T/ebp null mouse: thyroid-specific enhancer-binding protein is essential for the organogenesis of the thyroid, lung, ventral forebrain, and pituitary. Genes Dev* 1996, 10:60-69.
18. Apelqvist A, Ahlgren U, Edlund H: *Sonic hedgehog directs specialized mesoderm differentiation in the intestine and pancreas. Curr Biol* 1997, 7:801-804.
19. Chiang C et al.: *Cyclopia and defective axial patterning in mice lacking Sonic hedgehog gene function. Nature* 1996, 383: 407-413.
20. Chen H et al.: *Limb and kidney defects in Lmx1b mutant mice suggest and involvement of LMX1B in human nail patella syndrome. Nature Genetics* 1998, 19:51-55.

All of the above-cited references and publications are hereby incorporated by reference.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. A method of screening for an agent for inhibiting or reducing the proliferation or growth of lung cancer cells, comprising contacting lung cancer cells, which lung cancer cells are not squamous cell carcinoma cells, with an amount of an agent, wherein the agent is a small organic molecule, and determining, as compared to a control, whether the agent inhibits or attenuates hedgehog signaling and determining, as compared to a control, whether the agent inhibits or reduces cell proliferation or growth, wherein if the agent inhibits or attenuates the hedgehog signaling and inhibits or reduces cell proliferation or growth relative to the control, then an agent that inhibits or reduces the proliferation or growth of lung cancer cells is identified.

2. The method of claim 1, wherein the lung cancer cells are in culture.

3. The method of claim 1, wherein the lung cancer cells are in an animal.

* * * * *

UNITED STATES PATENT AND TRADEMARK OFFICE
CERTIFICATE OF CORRECTION

| | | |
|---|---|---|
| PATENT NO. | : 7,691,593 B2 | Page 1 of 1 |
| APPLICATION NO. | : 10/727195 | |
| DATED | : April 6, 2010 | |
| INVENTOR(S) | : Pepicelli et al. | |

It is certified that error appears in the above-identified patent and that said Letters Patent is hereby corrected as shown below:

In the Specification:

On page 1, column 1, lines 17-19, please replace the following paragraph under the heading GOVERNMENT FUNDING:

n--This invention was made with government support under NS033642 awarded by National Institutes of Health. The government has certain rights in the invention.--

Signed and Sealed this

Third Day of August, 2010

David J. Kappos
*Director of the United States Patent and Trademark Office*

SEQUENCE LISTING

```
<160> NUMBER OF SEQ ID NOS: 30

<210> SEQ ID NO 1
<211> LENGTH: 1277
<212> TYPE: DNA
<213> ORGANISM: Gallus sp.
<220> FEATURE:
<221> NAME/KEY: CDS
<222> LOCATION: (1)..(1275)

<400> SEQUENCE: 1
```

```
atg gtc gaa atg ctg ctg ttg aca aga att ctc ttg gtg ggc ttc atc        48
Met Val Glu Met Leu Leu Leu Thr Arg Ile Leu Leu Val Gly Phe Ile
 1               5                  10                  15 tgc gct ctt tta gtc tcc tct ggg ctg act tgt gga cca ggc agg ggc        96
Cys Ala Leu Leu Val Ser Ser Gly Leu Thr Cys Gly Pro Gly Arg Gly
                 20                  25                  30 att gga aaa agg agg cac ccc aaa aag ctg acc ccg tta gcc tat aag       144
Ile Gly Lys Arg Arg His Pro Lys Lys Leu Thr Pro Leu Ala Tyr Lys
             35                  40                  45 cag ttt att ccc aat gtg gca gag aag acc cta ggg gcc agt gga aga       192
Gln Phe Ile Pro Asn Val Ala Glu Lys Thr Leu Gly Ala Ser Gly Arg
 50                  55                  60 tat gaa ggg aag atc aca aga aac tcc gag aga ttt aaa gaa cta acc       240
Tyr Glu Gly Lys Ile Thr Arg Asn Ser Glu Arg Phe Lys Glu Leu Thr
 65                  70                  75                  80 cca aat tac aac cct gac att att ttt aag gat gaa gag aac acg gga       288
Pro Asn Tyr Asn Pro Asp Ile Ile Phe Lys Asp Glu Glu Asn Thr Gly
                 85                  90                  95 gct gac aga ctg atg act cag cgc tgc aag gac aag ctg aat gcc ctg       336
Ala Asp Arg Leu Met Thr Gln Arg Cys Lys Asp Lys Leu Asn Ala Leu
            100                 105                 110 gcg atc tcg gtg atg aac cag tgg ccc ggg gtg aag ctg cgg gtg acc       384
Ala Ile Ser Val Met Asn Gln Trp Pro Gly Val Lys Leu Arg Val Thr
        115                 120                 125 gag ggc tgg gac gag gat ggc cat cac tcc gag gaa tcg ctg cac tac       432
Glu Gly Trp Asp Glu Asp Gly His His Ser Glu Glu Ser Leu His Tyr
    130                 135                 140 gag ggt cgc gcc gtg gac atc acc acg tcg gat cgg gac cgc agc aag       480
Glu Gly Arg Ala Val Asp Ile Thr Thr Ser Asp Arg Asp Arg Ser Lys
145                 150                 155                 160 tac gga atg ctg gcc cgc ctc gcc gtc gag gcc ggc ttc gac tgg gtc       528
Tyr Gly Met Leu Ala Arg Leu Ala Val Glu Ala Gly Phe Asp Trp Val
                165                 170                 175 tac tac gag tcc aag gcg cac atc cac tgc tcc gtc aaa gca gaa aac       576
Tyr Tyr Glu Ser Lys Ala His Ile His Cys Ser Val Lys Ala Glu Asn
            180                 185                 190 tca gtg gca gcg aaa tca gga ggc tgc ttc cct ggc tca gcc aca gtg       624
Ser Val Ala Ala Lys Ser Gly Gly Cys Phe Pro Gly Ser Ala Thr Val
        195                 200                 205 cac ctg gag cat gga ggc acc aag ctg gtg aag gac ctg agc cct ggg       672
His Leu Glu His Gly Gly Thr Lys Leu Val Lys Asp Leu Ser Pro Gly
    210                 215                 220 gac cgc gtg ctg gct gct gac gcg gac ggc cgg ctg ctc tac agt gac       720
Asp Arg Val Leu Ala Ala Asp Ala Asp Gly Arg Leu Leu Tyr Ser Asp
225                 230                 235                 240 ttc ctc acc ttc ctc gac cgg atg gac agc tcc cga aag ctc ttc tac       768
Phe Leu Thr Phe Leu Asp Arg Met Asp Ser Ser Arg Lys Leu Phe Tyr
                245                 250                 255 gtc atc gag acg cgg cag ccc cgg gcc cgg ctg cta ctg acg gcg gcc       816
Val Ile Glu Thr Arg Gln Pro Arg Ala Arg Leu Leu Leu Thr Ala Ala
            260                 265                 270 cac ctg ctc ttt gtg gcc ccc cag cac aac cag tcg gag gcc aca ggg       864
His Leu Leu Phe Val Ala Pro Gln His Asn Gln Ser Glu Ala Thr Gly
        275                 280                 285 tcc acc agt ggc cag gcg ctc ttc gcc agc aac gtg aag cct ggc caa       912
Ser Thr Ser Gly Gln Ala Leu Phe Ala Ser Asn Val Lys Pro Gly Gln
    290                 295                 300 cgt gtc tat gtg ctg ggc gag ggc ggg cag cag ctg ctg ccg gcg tct       960
Arg Val Tyr Val Leu Gly Glu Gly Gly Gln Gln Leu Leu Pro Ala Ser
```

-continued

```
                  305                 310                 315                 320
gtc cac agc gtc tca ttg cgg gag gag gcg tcc gga gcc tac gcc cca       1008
Val His Ser Val Ser Leu Arg Glu Glu Ala Ser Gly Ala Tyr Ala Pro
                  325                 330                 335 ctc acc gcc cag ggc acc atc ctc atc aac cgg gtg ttg gcc tcc tgc       1056
Leu Thr Ala Gln Gly Thr Ile Leu Ile Asn Arg Val Leu Ala Ser Cys
              340                 345                 350 tac gcc gtc atc gag gag cac agt tgg gcc cat tgg gcc ttc gca cca       1104
Tyr Ala Val Ile Glu Glu His Ser Trp Ala His Trp Ala Phe Ala Pro
              355                 360                 365 ttc cgc ttg gct cag ggg ctg ctg gcc gcc ctc tgc cca gat ggg gcc       1152
Phe Arg Leu Ala Gln Gly Leu Leu Ala Ala Leu Cys Pro Asp Gly Ala
          370                 375                 380 atc cct act gcc gcc acc acc acc act ggc atc cat tgg tac tca cgg       1200
Ile Pro Thr Ala Ala Thr Thr Thr Thr Gly Ile His Trp Tyr Ser Arg
385                 390                 395                 400 ctc ctc tac cgc atc ggc agc tgg gtg ctg gat ggt gac gcg ctg cat       1248
Leu Leu Tyr Arg Ile Gly Ser Trp Val Leu Asp Gly Asp Ala Leu His
                  405                 410                 415 ccg ctg ggc atg gtg gca ccg gcc agc tg                                 1277
Pro Leu Gly Met Val Ala Pro Ala Ser
              420                 425

<210> SEQ ID NO 2
<211> LENGTH: 1190
<212> TYPE: DNA
<213> ORGANISM: Murine sp.
<220> FEATURE:
<221> NAME/KEY: CDS
<222> LOCATION: (1)..(1188)

<400> SEQUENCE: 2 atg gct ctg ccg gcc agt ctg ttg ccc ctg tgc tgc ttg gca ctc ttg         48
Met Ala Leu Pro Ala Ser Leu Leu Pro Leu Cys Cys Leu Ala Leu Leu
1               5                   10                  15 gca cta tct gcc cag agc tgc ggg ccg ggc cga gga ccg gtt ggc cgg         96
Ala Leu Ser Ala Gln Ser Cys Gly Pro Gly Arg Gly Pro Val Gly Arg
                20                  25                  30 cgg cgt tat gtg cgc aag caa ctt gtg cct ctg cta tac aag cag ttt        144
Arg Arg Tyr Val Arg Lys Gln Leu Val Pro Leu Leu Tyr Lys Gln Phe
            35                  40                  45 gtg ccc agt atg ccc gag cgg acc ctg ggc gcg agt ggg cca gcg gag        192
Val Pro Ser Met Pro Glu Arg Thr Leu Gly Ala Ser Gly Pro Ala Glu
        50                  55                  60 ggg agg gta aca agg ggg tcg gag cgc ttc cgg gac ctc gta ccc aac        240
Gly Arg Val Thr Arg Gly Ser Glu Arg Phe Arg Asp Leu Val Pro Asn
65                  70                  75                  80 tac aac ccc gac ata atc ttc aag gat gag gag aac agc ggc gca gac        288
Tyr Asn Pro Asp Ile Ile Phe Lys Asp Glu Glu Asn Ser Gly Ala Asp
                85                  90                  95 cgc ctg atg aca gag cgt tgc aaa gag cgg gtg aac gct cta gcc atc        336
Arg Leu Met Thr Glu Arg Cys Lys Glu Arg Val Asn Ala Leu Ala Ile
            100                 105                 110 gcg gtg atg aac atg tgg ccc gga gta cgc cta cgt gtg act gaa ggc        384
Ala Val Met Asn Met Trp Pro Gly Val Arg Leu Arg Val Thr Glu Gly
        115                 120                 125 tgg gac gag gac ggc cac cac gca cag gat tca ctc cac tac gaa ggc        432
Trp Asp Glu Asp Gly His His Ala Gln Asp Ser Leu His Tyr Glu Gly
    130                 135                 140 cgt gcc ttg gac atc acc acg tct gac cgt gac cgt aat aag tat ggt        480
Arg Ala Leu Asp Ile Thr Thr Ser Asp Arg Asp Arg Asn Lys Tyr Gly
```

```
ttg ttg gcg cgc cta gct gtg gaa gcc gga ttc gac tgg gtc tac tac      528
Leu Leu Ala Arg Leu Ala Val Glu Ala Gly Phe Asp Trp Val Tyr Tyr
            165                 170                 175 gag tcc cgc aac cac atc cac gta tcg gtc aaa gct gat aac tca ctg      576
Glu Ser Arg Asn His Ile His Val Ser Val Lys Ala Asp Asn Ser Leu
        180                 185                 190 gcg gtc cga gcc gga ggc tgc ttt ccg gga aat gcc acg gtg cgc ttg      624
Ala Val Arg Ala Gly Gly Cys Phe Pro Gly Asn Ala Thr Val Arg Leu
    195                 200                 205 cgg agc ggc gaa cgg aag ggg ctg agg gaa cta cat cgt ggt gac tgg      672
Arg Ser Gly Glu Arg Lys Gly Leu Arg Glu Leu His Arg Gly Asp Trp
210                 215                 220 gta ctg gcc gct gat gca gcg ggc cga gtg gta ccc acg cca gtg ctg      720
Val Leu Ala Ala Asp Ala Ala Gly Arg Val Val Pro Thr Pro Val Leu
225                 230                 235                 240 ctc ttc ctg gac cgg gat ctg cag cgc gcc gcc tcg ttc gtg gct gtg      768
Leu Phe Leu Asp Arg Asp Leu Gln Arg Arg Ala Ser Phe Val Ala Val
            245                 250                 255 gag acc gag cgg cct ccg cgc aaa ctg ttg ctc aca ccc tgg cat ctg      816
Glu Thr Glu Arg Pro Pro Arg Lys Leu Leu Leu Thr Pro Trp His Leu
        260                 265                 270 gtg ttc gct gct cgc ggg cca gcg cct gct cca ggt gac ttt gca ccg      864
Val Phe Ala Ala Arg Gly Pro Ala Pro Ala Pro Gly Asp Phe Ala Pro
    275                 280                 285 gtg ttc gcg cgc cgc tta cgt gct ggc gac tcg gtg ctg gct ccc ggc      912
Val Phe Ala Arg Arg Leu Arg Ala Gly Asp Ser Val Leu Ala Pro Gly
290                 295                 300 ggg gac gcg ctc cag ccg gcg cgc gta gcc cgc gtg gcg cgc gag gaa      960
Gly Asp Ala Leu Gln Pro Ala Arg Val Ala Arg Val Ala Arg Glu Glu
305                 310                 315                 320 gcc gtg ggc gtg ttc gca ccg ctc act gcg cac ggg acg ctg ctg gtc     1008
Ala Val Gly Val Phe Ala Pro Leu Thr Ala His Gly Thr Leu Leu Val
            325                 330                 335 aac gac gtc ctc gcc tcc tgc tac gcg gtt cta gag agt cac cag tgg     1056
Asn Asp Val Leu Ala Ser Cys Tyr Ala Val Leu Glu Ser His Gln Trp
        340                 345                 350 gcc cac cgc gcc ttc gcc cct ttg cgg ctg ctg cac gcg ctc ggg gct     1104
Ala His Arg Ala Phe Ala Pro Leu Arg Leu Leu His Ala Leu Gly Ala
    355                 360                 365 ctg ctc cct ggg ggt gca gtc cag ccg act ggc atg cat tgg tac tct     1152
Leu Leu Pro Gly Gly Ala Val Gln Pro Thr Gly Met His Trp Tyr Ser
370                 375                 380 cgc ctc ctt tac cgc ttg gcc gag gag tta atg ggc tg                  1190
Arg Leu Leu Tyr Arg Leu Ala Glu Glu Leu Met Gly
385                 390                 395
```

<210> SEQ ID NO 3
<211> LENGTH: 1281
<212> TYPE: DNA
<213> ORGANISM: Murine sp.
<220> FEATURE:
<221> NAME/KEY: CDS
<222> LOCATION: (1)..(1233)

<400> SEQUENCE: 3

```
atg tct ccc gcc tgg ctc cgg ccc cga ctg cgg ttc tgt ctg ttc ctg       48
Met Ser Pro Ala Trp Leu Arg Pro Arg Leu Arg Phe Cys Leu Phe Leu
1               5                   10                  15 ctg ctg ctg ctt ctg gtg ccg gcg gcg cgg ggc tgc ggg ccg ggc cgg       96
Leu Leu Leu Leu Leu Val Pro Ala Ala Arg Gly Cys Gly Pro Gly Arg
```

-continued

```
                  20                    25                     30
gtg gtg ggc agc cgc cgg agg ccg cct cgc aag ctc gtg cct ctt gcc    144
Val Val Gly Ser Arg Arg Arg Pro Pro Arg Lys Leu Val Pro Leu Ala
             35                    40                     45 tac aag cag ttc agc ccc aac gtg ccg gag aag acc ctg ggc gcc agc    192
Tyr Lys Gln Phe Ser Pro Asn Val Pro Glu Lys Thr Leu Gly Ala Ser
 50                    55                     60 ggg cgc tac gaa ggc aag atc gcg cgc agc tct gag cgc ttc aaa gag    240
Gly Arg Tyr Glu Gly Lys Ile Ala Arg Ser Ser Glu Arg Phe Lys Glu
 65                    70                     75                 80 ctc acc ccc aac tac aat ccc gac atc atc ttc aag gac gag gag aac    288
Leu Thr Pro Asn Tyr Asn Pro Asp Ile Ile Phe Lys Asp Glu Glu Asn
                     85                     90                     95 acg ggt gcc gac cgc ctc atg acc cag cgc tgc aag gac cgt ctg aac    336
Thr Gly Ala Asp Arg Leu Met Thr Gln Arg Cys Lys Asp Arg Leu Asn
             100                    105                    110 tca ctg gcc atc tct gtc atg aac cag tgg cct ggt gtg aaa ctg cgg    384
Ser Leu Ala Ile Ser Val Met Asn Gln Trp Pro Gly Val Lys Leu Arg
         115                    120                    125 gtg acc gaa ggc cgg gat gaa gat ggc cat cac tca gag gag tct tta    432
Val Thr Glu Gly Arg Asp Glu Asp Gly His His Ser Glu Glu Ser Leu
 130                    135                    140 cac tat gag ggc cgc gcg gtg gat atc acc acc tca gac cgt gac cga    480
His Tyr Glu Gly Arg Ala Val Asp Ile Thr Thr Ser Asp Arg Asp Arg
145                    150                    155                    160 aat aag tat gga ctg ctg gcg cgc tta gca gtg gag gcc ggc ttc gac    528
Asn Lys Tyr Gly Leu Leu Ala Arg Leu Ala Val Glu Ala Gly Phe Asp
                     165                    170                    175 tgg gtg tat tac gag tcc aag gcc cac gtg cat tgc tct gtc aag tct    576
Trp Val Tyr Tyr Glu Ser Lys Ala His Val His Cys Ser Val Lys Ser
             180                    185                    190 gag cat tcg gcc gct gcc aag aca ggt ggc tgc ttt cct gcc gga gcc    624
Glu His Ser Ala Ala Ala Lys Thr Gly Gly Cys Phe Pro Ala Gly Ala
         195                    200                    205 cag gtg cgc cta gag aac ggg gag cgt gtg gcc ctg tca gct gta aag    672
Gln Val Arg Leu Glu Asn Gly Glu Arg Val Ala Leu Ser Ala Val Lys
 210                    215                    220 cca gga gac cgg gtg ctg gcc atg ggg gag gat ggg acc ccc acc ttc    720
Pro Gly Asp Arg Val Leu Ala Met Gly Glu Asp Gly Thr Pro Thr Phe
225                    230                    235                    240 agt gat gtg ctt att ttc ctg gac cgc gag cca aac cgg ctg aga gct    768
Ser Asp Val Leu Ile Phe Leu Asp Arg Glu Pro Asn Arg Leu Arg Ala
                     245                    250                    255 ttc cag gtc atc gag act cag gat cct ccg cgt cgg ctg gcg ctc acg    816
Phe Gln Val Ile Glu Thr Gln Asp Pro Pro Arg Arg Leu Ala Leu Thr
             260                    265                    270 cct gcc cac ctg ctc ttc att gcg gac aat cat aca gaa cca gca gcc    864
Pro Ala His Leu Leu Phe Ile Ala Asp Asn His Thr Glu Pro Ala Ala
         275                    280                    285 cac ttc cgg gcc aca ttt gcc agc cat gtg caa cca ggc caa tat gtg    912
His Phe Arg Ala Thr Phe Ala Ser His Val Gln Pro Gly Gln Tyr Val
 290                    295                    300 ctg gta tca ggg gta cca ggc ctc cag cct gct cgg gtg gca gct gtc    960
Leu Val Ser Gly Val Pro Gly Leu Gln Pro Ala Arg Val Ala Ala Val
305                    310                    315                    320 tcc acc cac gtg gcc ctt ggg tcc tat gct cct ctc aca agg cat ggg    1008
Ser Thr His Val Ala Leu Gly Ser Tyr Ala Pro Leu Thr Arg His Gly
                     325                    330                    335 aca ctt gtg gtg gag gat gtg gtg gcc tcc tgc ttt gca gct gtg gct    1056
```

```
                                                -continued

Thr Leu Val Val Glu Asp Val Val Ala Ser Cys Phe Ala Ala Val Ala
            340                 345                 350 gac cac cat ctg gct cag ttg gcc ttc tgg ccc ctg cga ctg ttt ccc        1104
Asp His His Leu Ala Gln Leu Ala Phe Trp Pro Leu Arg Leu Phe Pro
        355                 360                 365 agt ttg gca tgg ggc agc tgg acc cca agt gag ggt gtt cac tcc tac        1152
Ser Leu Ala Trp Gly Ser Trp Thr Pro Ser Glu Gly Val His Ser Tyr
    370                 375                 380 cct cag atg ctc tac cgc ctg ggg cgt ctc ttg cta gaa gag agc acc        1200
Pro Gln Met Leu Tyr Arg Leu Gly Arg Leu Leu Leu Glu Glu Ser Thr
385                 390                 395                 400 ttc cat cca ctg ggc atg tct ggg gca gga agc tgaagggact ctaaccactg      1253
Phe His Pro Leu Gly Met Ser Gly Ala Gly Ser
                405                 410 ccctcctgga actgctgtgc gtggatcc                                         1281

<210> SEQ ID NO 4
<211> LENGTH: 1313
<212> TYPE: DNA
<213> ORGANISM: Murine sp.
<220> FEATURE:
<221> NAME/KEY: CDS
<222> LOCATION: (1)..(1311)

<400> SEQUENCE: 4 atg ctg ctg ctg ctg gcc aga tgt ttt ctg gtg atc ctt gct tcc tcg         48
Met Leu Leu Leu Leu Ala Arg Cys Phe Leu Val Ile Leu Ala Ser Ser
1               5                   10                  15 ctg ctg gtg tgc ccc ggg ctg gcc tgt ggg ccc ggc agg ggg ttt gga         96
Leu Leu Val Cys Pro Gly Leu Ala Cys Gly Pro Gly Arg Gly Phe Gly
                20                  25                  30 aag agg cgg cac ccc aaa aag ctg acc cct tta gcc tac aag cag ttt        144
Lys Arg Arg His Pro Lys Lys Leu Thr Pro Leu Ala Tyr Lys Gln Phe
            35                  40                  45 att ccc aac gta gcc gag aag acc cta ggg gcc agc ggc aga tat gaa        192
Ile Pro Asn Val Ala Glu Lys Thr Leu Gly Ala Ser Gly Arg Tyr Glu
        50                  55                  60 ggg aag atc aca aga aac tcc gaa cga ttt aag gaa ctc acc ccc aat        240
Gly Lys Ile Thr Arg Asn Ser Glu Arg Phe Lys Glu Leu Thr Pro Asn
65                  70                  75                  80 tac aac ccc gac atc ata ttt aag gat gag gaa aac acg gga gca gac        288
Tyr Asn Pro Asp Ile Ile Phe Lys Asp Glu Glu Asn Thr Gly Ala Asp
                85                  90                  95 cgg ctg atg act cag agg tgc aaa gac aag tta aat gcc ttg gcc atc        336
Arg Leu Met Thr Gln Arg Cys Lys Asp Lys Leu Asn Ala Leu Ala Ile
                100                 105                 110 tct gtg atg aac cag tgg cct gga gtg agg ctg cga gtg acc gag ggc        384
Ser Val Met Asn Gln Trp Pro Gly Val Arg Leu Arg Val Thr Glu Gly
            115                 120                 125 tgg gat gag gac ggc cat cat tca gag gag tct cta cac tat gag ggt        432
Trp Asp Glu Asp Gly His His Ser Glu Glu Ser Leu His Tyr Glu Gly
        130                 135                 140 cga gca gtg gac atc acc acg tcc gac cgg gac cgc agc aag tac ggc        480
Arg Ala Val Asp Ile Thr Thr Ser Asp Arg Asp Arg Ser Lys Tyr Gly
145                 150                 155                 160 atg ctg gct cgc ctg gct gtg gaa gca ggt ttc gac tgg gtc tac tat        528
Met Leu Ala Arg Leu Ala Val Glu Ala Gly Phe Asp Trp Val Tyr Tyr
                165                 170                 175 gaa tcc aaa gct cac atc cac tgt tct gtg aaa gca gag aac tcc gtg        576
Glu Ser Lys Ala His Ile His Cys Ser Val Lys Ala Glu Asn Ser Val
                180                 185                 190
```

```
gcg gcc aaa tcc ggc ggc tgt ttc ccg gga tcc gcc acc gtg cac ctg      624
Ala Ala Lys Ser Gly Gly Cys Phe Pro Gly Ser Ala Thr Val His Leu
        195                 200                 205 gag cag ggc ggc acc aag ctg gtg aag gac tta cgt ccc gga gac cgc      672
Glu Gln Gly Gly Thr Lys Leu Val Lys Asp Leu Arg Pro Gly Asp Arg
210                 215                 220 gtg ctg gcg gct gac gac cag ggc cgg ctg ctg tac agc gac ttc ctc      720
Val Leu Ala Ala Asp Asp Gln Gly Arg Leu Leu Tyr Ser Asp Phe Leu
225                 230                 235                 240 acc ttc ctg gac cgc gac gaa ggc gcc aag aag gtc ttc tac gtg atc      768
Thr Phe Leu Asp Arg Asp Glu Gly Ala Lys Lys Val Phe Tyr Val Ile
                245                 250                 255 gag acg ctg gag ccg cgc gag cgc ctg ctc acc gcc gcg cac ctg          816
Glu Thr Leu Glu Pro Arg Glu Arg Leu Leu Thr Ala Ala His Leu
            260                 265                 270 ctc ttc gtg gcg ccg cac aac gac tcg ggg ccc acg ccc ggg cca agc      864
Leu Phe Val Ala Pro His Asn Asp Ser Gly Pro Thr Pro Gly Pro Ser
        275                 280                 285 gcg ctc ttt gcc agc cgc gtg cgc ccc ggg cag cgc gtg tac gtg gtg      912
Ala Leu Phe Ala Ser Arg Val Arg Pro Gly Gln Arg Val Tyr Val Val
290                 295                 300 gct gaa cgc ggc ggg gac cgc cgg ctg ctg ccc gcc gcg gtg cac agc      960
Ala Glu Arg Gly Gly Asp Arg Arg Leu Leu Pro Ala Ala Val His Ser
305                 310                 315                 320 gtg acg ctg cga gag gag gag gcg ggc gcg tac gcg ccg ctc acg gcg     1008
Val Thr Leu Arg Glu Glu Glu Ala Gly Ala Tyr Ala Pro Leu Thr Ala
                325                 330                 335 cac ggc acc att ctc atc aac cgg gtg ctc gcc tcg tgc tac gct gtc     1056
His Gly Thr Ile Leu Ile Asn Arg Val Leu Ala Ser Cys Tyr Ala Val
            340                 345                 350 atc gag gag cac agc tgg gca cac cgg gcc ttc gcg cct ttc cgc ctg     1104
Ile Glu Glu His Ser Trp Ala His Arg Ala Phe Ala Pro Phe Arg Leu
        355                 360                 365 gcg cac gcg ctg ctg gcc gcg ctg gca ccc gcc cgc acg gac ggc ggg     1152
Ala His Ala Leu Leu Ala Ala Leu Ala Pro Ala Arg Thr Asp Gly Gly
370                 375                 380 ggc ggg ggc agc atc cct gca gcg caa tct gca acg gaa gcg agg ggc     1200
Gly Gly Gly Ser Ile Pro Ala Ala Gln Ser Ala Thr Glu Ala Arg Gly
385                 390                 395                 400 gcg gag ccg act gcg ggc atc cac tgg tac tcg cag ctg ctc tac cac     1248
Ala Glu Pro Thr Ala Gly Ile His Trp Tyr Ser Gln Leu Leu Tyr His
                405                 410                 415 att ggc acc tgg ctg ttg gac agc gag acc atg cat ccc ttg gga atg     1296
Ile Gly Thr Trp Leu Leu Asp Ser Glu Thr Met His Pro Leu Gly Met
            420                 425                 430 gcg gtc aag tcc agc tg                                              1313
Ala Val Lys Ser Ser
        435

<210> SEQ ID NO 5
<211> LENGTH: 1256
<212> TYPE: DNA
<213> ORGANISM: Brachydanio rerio
<220> FEATURE:
<221> NAME/KEY: CDS
<222> LOCATION: (1)..(1254)

<400> SEQUENCE: 5 atg cgg ctt ttg acg aga gtg ctg ctg gtg tct ctt ctc act ctg tcc       48
Met Arg Leu Leu Thr Arg Val Leu Leu Val Ser Leu Leu Thr Leu Ser
1               5                  10                  15
```

-continued

| | |
|---|---|
| ttg gtg gtg tcc gga ctg gcc tgc ggt cct ggc aga ggc tac ggc aga<br>Leu Val Val Ser Gly Leu Ala Cys Gly Pro Gly Arg Gly Tyr Gly Arg<br>              20                   25                   30 | 96 |
| aga aga cat ccg aag aag ctg aca cct ctc gcc tac aag cag ttc ata<br>Arg Arg His Pro Lys Lys Leu Thr Pro Leu Ala Tyr Lys Gln Phe Ile<br>              35                   40                   45 | 144 |
| cct aat gtc gcg gag aag acc tta ggg gcc agc ggc aga tac gag ggc<br>Pro Asn Val Ala Glu Lys Thr Leu Gly Ala Ser Gly Arg Tyr Glu Gly<br>50                   55                   60 | 192 |
| aag ata acg cgc aat tcg gag aga ttt aaa gaa ctt act cca aat tac<br>Lys Ile Thr Arg Asn Ser Glu Arg Phe Lys Glu Leu Thr Pro Asn Tyr<br>65                   70                   75                   80 | 240 |
| aat ccc gac att atc ttt aag gat gag gag aac acg gga gcg gac agg<br>Asn Pro Asp Ile Ile Phe Lys Asp Glu Glu Asn Thr Gly Ala Asp Arg<br>              85                   90                   95 | 288 |
| ctc atg aca cag aga tgc aaa gac aag ctg aac tcg ctg gcc atc tct<br>Leu Met Thr Gln Arg Cys Lys Asp Lys Leu Asn Ser Leu Ala Ile Ser<br>            100                 105               110 | 336 |
| gta atg aac cac tgg cca ggg gtt aag ctg cgt gtg aca gag ggc tgg<br>Val Met Asn His Trp Pro Gly Val Lys Leu Arg Val Thr Glu Gly Trp<br>            115                 120               125 | 384 |
| gat gag gac ggt cac cat ttt gaa gaa tca ctc cac tac gag gga aga<br>Asp Glu Asp Gly His His Phe Glu Glu Ser Leu His Tyr Glu Gly Arg<br>130                 135               140 | 432 |
| gct gtt gat att acc acc tct gac cga gac aag agc aaa tac ggg aca<br>Ala Val Asp Ile Thr Thr Ser Asp Arg Asp Lys Ser Lys Tyr Gly Thr<br>145                 150               155               160 | 480 |
| ctg tct cgc cta gct gtg gag gct gga ttt gac tgg gtc tat tac gag<br>Leu Ser Arg Leu Ala Val Glu Ala Gly Phe Asp Trp Val Tyr Tyr Glu<br>                 165               170               175 | 528 |
| tcc aaa gcc cac att cat tgc tct gtc aaa gca gaa aat tcg gtt gct<br>Ser Lys Ala His Ile His Cys Ser Val Lys Ala Glu Asn Ser Val Ala<br>            180                 185               190 | 576 |
| gcg aaa tct ggg ggc tgt ttc cca ggt tcg gct ctg gtc tcg ctc cag<br>Ala Lys Ser Gly Gly Cys Phe Pro Gly Ser Ala Leu Val Ser Leu Gln<br>            195                 200               205 | 624 |
| gac gga gga cag aag gcc gtg aag gac ctg aac ccc gga gac aag gtg<br>Asp Gly Gly Gln Lys Ala Val Lys Asp Leu Asn Pro Gly Asp Lys Val<br>210                 215               220 | 672 |
| ctg gcg gca gac agc gcg gga aac ctg gtg ttc agc gac ttc atc atg<br>Leu Ala Ala Asp Ser Ala Gly Asn Leu Val Phe Ser Asp Phe Ile Met<br>225                 230               235               240 | 720 |
| ttc aca gac cga gac tcc acg acg cga cgt gtg ttt tac gtc ata gaa<br>Phe Thr Asp Arg Asp Ser Thr Thr Arg Arg Val Phe Tyr Val Ile Glu<br>                 245               250               255 | 768 |
| acg caa gaa ccc gtt gaa aag atc acc ctc acc gcc gct cac ctc ctt<br>Thr Gln Glu Pro Val Glu Lys Ile Thr Leu Thr Ala Ala His Leu Leu<br>            260                 265               270 | 816 |
| ttt gtc ctc gac aac tca acg gaa gat ctc cac acc atg acc gcc gcg<br>Phe Val Leu Asp Asn Ser Thr Glu Asp Leu His Thr Met Thr Ala Ala<br>            275                 280               285 | 864 |
| tat gcc agc agt gtc aga gcc gga caa aag gtg atg gtt gtt gat gat<br>Tyr Ala Ser Ser Val Arg Ala Gly Gln Lys Val Met Val Val Asp Asp<br>            290                 295               300 | 912 |
| agc ggt cag ctt aaa tct gtc atc gtg cag cgg ata tac acg gag gag<br>Ser Gly Gln Leu Lys Ser Val Ile Val Gln Arg Ile Tyr Thr Glu Glu<br>305                 310               315               320 | 960 |
| cag cgg ggc tcg ttc gca cca gtg act gca cat ggg acc att gtg gtc<br>Gln Arg Gly Ser Phe Ala Pro Val Thr Ala His Gly Thr Ile Val Val | 1008 |

```
                        325                 330                 335
gac aga ata ctg gcg tcc tgt tac gcc gta ata gag gac cag ggg ctt      1056
Asp Arg Ile Leu Ala Ser Cys Tyr Ala Val Ile Glu Asp Gln Gly Leu
            340                 345                 350 gcg cat ttg gcc ttc gcg ccc gcc agg ctc tat tat tac gtg tca tca      1104
Ala His Leu Ala Phe Ala Pro Ala Arg Leu Tyr Tyr Tyr Val Ser Ser
                355                 360                 365 ttc ctg tcc ccc aaa act cca gca gtc ggt cca atg cga ctt tac aac      1152
Phe Leu Ser Pro Lys Thr Pro Ala Val Gly Pro Met Arg Leu Tyr Asn
        370                 375                 380 agg agg ggg tcc act ggt act cca ggc tcc tgt cat caa atg gga acg      1200
Arg Arg Gly Ser Thr Gly Thr Pro Gly Ser Cys His Gln Met Gly Thr
385                 390                 395                 400 tgg ctt ttg gac agc aac atg ctt cat cct ttg ggg atg tca gta aac      1248
Trp Leu Leu Asp Ser Asn Met Leu His Pro Leu Gly Met Ser Val Asn
                405                 410                 415 tca agc tg                                                           1256
Ser Ser <210> SEQ ID NO 6
<211> LENGTH: 1425
<212> TYPE: DNA
<213> ORGANISM: Homo sapiens
<220> FEATURE:
<221> NAME/KEY: CDS
<222> LOCATION: (1)..(1425)
<223> OTHER INFORMATION: "nnn" encoding "Xaa" at position 1387-1389 may
      be a, t, c, g, other or unknown

<400> SEQUENCE: 6 atg ctg ctg ctg gcg aga tgt ctg ctg cta gtc ctc gtc tcc tcg ctg       48
Met Leu Leu Leu Ala Arg Cys Leu Leu Leu Val Leu Val Ser Ser Leu
1               5                   10                  15 ctg gta tgc tcg gga ctg gcg tgc gga ccg ggc agg ggg ttc ggg aag       96
Leu Val Cys Ser Gly Leu Ala Cys Gly Pro Gly Arg Gly Phe Gly Lys
                20                  25                  30 agg agg cac ccc aaa aag ctg acc cct tta gcc tac aag cag ttt atc      144
Arg Arg His Pro Lys Lys Leu Thr Pro Leu Ala Tyr Lys Gln Phe Ile
            35                  40                  45 ccc aat gtg gcc gag aag acc cta ggc gcc agc gga agg tat gaa ggg      192
Pro Asn Val Ala Glu Lys Thr Leu Gly Ala Ser Gly Arg Tyr Glu Gly
        50                  55                  60 aag atc tcc aga aac tcc gag cga ttt aag gaa ctc acc ccc aat tac      240
Lys Ile Ser Arg Asn Ser Glu Arg Phe Lys Glu Leu Thr Pro Asn Tyr
65                  70                  75                  80 aac ccc gac atc ata ttt aag gat gaa gaa aac acc gga gcg gac agg      288
Asn Pro Asp Ile Ile Phe Lys Asp Glu Glu Asn Thr Gly Ala Asp Arg
                85                  90                  95 ctg atg act cag agg tgt aag gac aag ttg aac gct ttg gcc atc tcg      336
Leu Met Thr Gln Arg Cys Lys Asp Lys Leu Asn Ala Leu Ala Ile Ser
            100                 105                 110 gtg atg aac cag tgg cca gga gtg aaa ctg cgg gtg acc gag ggc tgg      384
Val Met Asn Gln Trp Pro Gly Val Lys Leu Arg Val Thr Glu Gly Trp
        115                 120                 125 gac gaa gat ggc cac cac tca gag gag tct ctg cac tac gag ggc cgc      432
Asp Glu Asp Gly His His Ser Glu Glu Ser Leu His Tyr Glu Gly Arg
        130                 135                 140 gca gtg gac atc acc acg tct gac cgc gac cgc agc aag tac ggc atg      480
Ala Val Asp Ile Thr Thr Ser Asp Arg Asp Arg Ser Lys Tyr Gly Met
145                 150                 155                 160 ctg gcc cgc ctg gcg gtg gag gcc ggc ttc gac tgg gtg tac tac gag      528
```

-continued

```
          Leu Ala Arg Leu Ala Val Glu Ala Gly Phe Asp Trp Val Tyr Tyr Glu
                      165                 170                 175 tcc aag gca cat atc cac tgc tcg gtg aaa gca gag aac tcg gtg gcg        576
Ser Lys Ala His Ile His Cys Ser Val Lys Ala Glu Asn Ser Val Ala
            180                 185                 190 gcc aaa tcg gga ggc tgc ttc ccg ggc tcg gcc acg gtg cac ctg gag        624
Ala Lys Ser Gly Gly Cys Phe Pro Gly Ser Ala Thr Val His Leu Glu
        195                 200                 205 cag ggc ggc acc aag ctg gtg aag gac ctg agc ccc ggg gac cgc gtg        672
Gln Gly Gly Thr Lys Leu Val Lys Asp Leu Ser Pro Gly Asp Arg Val
    210                 215                 220 ctg gcg gcg gac gac cag ggc cgg ctg ctc tac agc gac ttc ctc act        720
Leu Ala Ala Asp Asp Gln Gly Arg Leu Leu Tyr Ser Asp Phe Leu Thr
225                 230                 235                 240 ttc ctg gac cgc gac gac ggc gcc aag aag gtc ttc tac gtg atc gag        768
Phe Leu Asp Arg Asp Asp Gly Ala Lys Lys Val Phe Tyr Val Ile Glu
                245                 250                 255 acg cgg gag ccg cgc gag cgc ctg ctc acc gcc gcg cac ctg ctc            816
Thr Arg Glu Pro Arg Glu Arg Leu Leu Thr Ala Ala His Leu Leu
            260                 265                 270 ttt gtg gcg ccg cac aac gac tcg gcc acc ggg gag ccc gag gcg tcc        864
Phe Val Ala Pro His Asn Asp Ser Ala Thr Gly Glu Pro Glu Ala Ser
        275                 280                 285 tcg ggc tcg ggg ccg cct tcc ggg ggc gca ctg ggg cct cgg gcg ctg        912
Ser Gly Ser Gly Pro Pro Ser Gly Gly Ala Leu Gly Pro Arg Ala Leu
    290                 295                 300 ttc gcc agc cgc gtg cgc ccg ggc cag cgc gtg tac gtg gtg gcc gag        960
Phe Ala Ser Arg Val Arg Pro Gly Gln Arg Val Tyr Val Val Ala Glu
305                 310                 315                 320 cgt gac ggg gac cgc cgg ctc ctg ccc gcc gct gtg cac agc gtg acc       1008
Arg Asp Gly Asp Arg Arg Leu Leu Pro Ala Ala Val His Ser Val Thr
                325                 330                 335 cta agc gag gag gcc gcg ggc gcc tac gcg ccg ctc acg gcc cag ggc       1056
Leu Ser Glu Glu Ala Ala Gly Ala Tyr Ala Pro Leu Thr Ala Gln Gly
            340                 345                 350 acc att ctc atc aac cgg gtg ctg gcc tcg tgc tac gcg gtc atc gag       1104
Thr Ile Leu Ile Asn Arg Val Leu Ala Ser Cys Tyr Ala Val Ile Glu
        355                 360                 365 gag cac agc tgg gcg cac cgg gcc ttc gcg ccc ttc cgc ctg gcg cac       1152
Glu His Ser Trp Ala His Arg Ala Phe Ala Pro Phe Arg Leu Ala His
    370                 375                 380 gcg ctc ctg gct gca ctg gcg ccc gcg cgc acg gac cgc ggg ggg gac       1200
Ala Leu Leu Ala Ala Leu Ala Pro Ala Arg Thr Asp Arg Gly Gly Asp
385                 390                 395                 400 agc ggc ggc ggg gac cgc ggg ggc ggc ggc aga gta gcc cta acc            1248
Ser Gly Gly Gly Asp Arg Gly Gly Gly Gly Arg Val Ala Leu Thr
                405                 410                 415 gct cca ggt gct gcc gac gct ccg ggt gcg ggg gcc acc gcg ggc atc       1296
Ala Pro Gly Ala Ala Asp Ala Pro Gly Ala Gly Ala Thr Ala Gly Ile
            420                 425                 430 cac tgg tac tcg cag ctg ctc tac caa ata ggc acc tgg ctc ctg gac       1344
His Trp Tyr Ser Gln Leu Leu Tyr Gln Ile Gly Thr Trp Leu Leu Asp
        435                 440                 445 agc gag gcc ctg cac ccg ctg ggc atg gcg gtc aag tcc agc nnn agc       1392
Ser Glu Ala Leu His Pro Leu Gly Met Ala Val Lys Ser Ser Xaa Ser
    450                 455                 460 cgg ggg gcc ggg gga ggg gcg cgg gag ggg gcc                           1425
Arg Gly Ala Gly Gly Gly Ala Arg Glu Gly Ala
465                 470                 475
```

<210> SEQ ID NO 7
<211> LENGTH: 1622
<212> TYPE: DNA
<213> ORGANISM: Homo sapiens
<220> FEATURE:
<221> NAME/KEY: CDS
<222> LOCATION: (51)..(1283)

<400> SEQUENCE: 7

| | | |
|---|---|---|
| catcagccca ccaggagacc tcgcccgccg ctcccccggg ctccccggcc atg tct<br>                                                                                                                          Met Ser<br>                                                                                                                           1 | | 56 |
| ccc gcc cgg ctc cgg ccc cga ctg cac ttc tgc ctg gtc ctg ttg ctg<br>Pro Ala Arg Leu Arg Pro Arg Leu His Phe Cys Leu Val Leu Leu Leu<br>             5                     10                     15 | | 104 |
| ctg ctg gtg gtg ccc gcg gca tgg ggc tgc ggg ccg gtc ggg gtg gtg<br>Leu Leu Val Val Pro Ala Ala Trp Gly Cys Gly Pro Val Gly Val Val<br>      20                    25                     30 | | 152 |
| ggc agc cgc cgg cga ccg cca cgc aaa ctc gtc ccg ctc gcc tac aag<br>Gly Ser Arg Arg Arg Pro Pro Arg Lys Leu Val Pro Leu Ala Tyr Lys<br>35                     40                     45                     50 | | 200 |
| cag ttc agc ccc aat gtg ccc gag aag acc ctg ggc gcc agc gga cgc<br>Gln Phe Ser Pro Asn Val Pro Glu Lys Thr Leu Gly Ala Ser Gly Arg<br>                   55                     60                     65 | | 248 |
| tat gaa ggc aag atc gct cgc agc tcc gag cgc ttc aag gag ctc acc<br>Tyr Glu Gly Lys Ile Ala Arg Ser Ser Glu Arg Phe Lys Glu Leu Thr<br>               70                     75                     80 | | 296 |
| ccc aat tac aat cca gac atc atc ttc aag gac gag gag aac aca ggc<br>Pro Asn Tyr Asn Pro Asp Ile Ile Phe Lys Asp Glu Glu Asn Thr Gly<br>          85                     90                     95 | | 344 |
| gcc gac cgc ctc atg acc cag cgc tgc aag gac cgc ctg aac tcg ctg<br>Ala Asp Arg Leu Met Thr Gln Arg Cys Lys Asp Arg Leu Asn Ser Leu<br>100                    105                    110 | | 392 |
| gct atc tcg gtg atg aac cag tgg ccc ggt gtg aag ctg cgg gtg acc<br>Ala Ile Ser Val Met Asn Gln Trp Pro Gly Val Lys Leu Arg Val Thr<br>115                    120                    125                    130 | | 440 |
| gag ggc tgg gac gag gac ggc cac cac tca gag gag tcc ctg cat tat<br>Glu Gly Trp Asp Glu Asp Gly His His Ser Glu Glu Ser Leu His Tyr<br>                  135                    140                    145 | | 488 |
| gag ggc cgc gcg gtg gac atc acc aca tca gac cgc gac cgc aat aag<br>Glu Gly Arg Ala Val Asp Ile Thr Thr Ser Asp Arg Asp Arg Asn Lys<br>             150                    155                    160 | | 536 |
| tat gga ctg ctg gcg cgc ttg gca gtg gag gcc ggc ttt gac tgg gtg<br>Tyr Gly Leu Leu Ala Arg Leu Ala Val Glu Ala Gly Phe Asp Trp Val<br>          165                    170                    175 | | 584 |
| tat tac gag tca aag gcc cac gtg cat tgc tcc gtc aag tcc gag cac<br>Tyr Tyr Glu Ser Lys Ala His Val His Cys Ser Val Lys Ser Glu His<br>180                    185                    190 | | 632 |
| tcg gcc gca gcc aag acg ggc ggc tgc ttc cct gcc gga gcc cag gta<br>Ser Ala Ala Ala Lys Thr Gly Gly Cys Phe Pro Ala Gly Ala Gln Val<br>195                    200                    205                    210 | | 680 |
| cgc ctg gag agt ggg gcg cgt gtg gcc ttg tca gcc gtg agg ccg gga<br>Arg Leu Glu Ser Gly Ala Arg Val Ala Leu Ser Ala Val Arg Pro Gly<br>                  215                    220                    225 | | 728 |
| gac cgt gtg ctg gcc atg ggg gag gat ggg agc ccc acc ttc agc gat<br>Asp Arg Val Leu Ala Met Gly Glu Asp Gly Ser Pro Thr Phe Ser Asp<br>             230                    235                    240 | | 776 |
| gtg ctc att ttc ctg gac cgc gag ccc cac agg ctg aga gcc ttc cag<br>Val Leu Ile Phe Leu Asp Arg Glu Pro His Arg Leu Arg Ala Phe Gln<br>          245                    250                    255 | | 824 |

```
gtc atc gag act cag gac ccc cca cgc cgc ctg gca ctc aca ccc gct      872
Val Ile Glu Thr Gln Asp Pro Pro Arg Arg Leu Ala Leu Thr Pro Ala
    260                 265                 270 cac ctg ctc ttt acg gct gac aat cac acg gag ccg gca gcc cgc ttc      920
His Leu Leu Phe Thr Ala Asp Asn His Thr Glu Pro Ala Ala Arg Phe
275                 280                 285                 290 cgg gcc aca ttt gcc agc cac gtg cag cct ggc cag tac gtg ctg gtg      968
Arg Ala Thr Phe Ala Ser His Val Gln Pro Gly Gln Tyr Val Leu Val
                295                 300                 305 gct ggg gtg cca ggc ctg cag cct gcc cgc gtg gca gct gtc tct aca     1016
Ala Gly Val Pro Gly Leu Gln Pro Ala Arg Val Ala Ala Val Ser Thr
310                 315                 320 cac gtg gcc ctc ggg gcc tac gcc ccg ctc aca aag cat ggg aca ctg     1064
His Val Ala Leu Gly Ala Tyr Ala Pro Leu Thr Lys His Gly Thr Leu
    325                 330                 335 gtg gtg gag gat gtg gtg gca tcc tgc ttc gcg gcc gtg gct gac cac     1112
Val Val Glu Asp Val Val Ala Ser Cys Phe Ala Ala Val Ala Asp His
340                 345                 350 cac ctg gct cag ttg gcc ttc tgg ccc ctg aga ctc ttt cac agc ttg     1160
His Leu Ala Gln Leu Ala Phe Trp Pro Leu Arg Leu Phe His Ser Leu
355                 360                 365                 370 gca tgg ggc agc tgg acc ccg ggg gag ggt gtg cat tgg tac ccc cag     1208
Ala Trp Gly Ser Trp Thr Pro Gly Glu Gly Val His Trp Tyr Pro Gln
                375                 380                 385 ctc ctc tac cgc ctg ggg cgt ctc ctg cta gaa gag ggc agc ttc cac     1256
Leu Leu Tyr Arg Leu Gly Arg Leu Leu Leu Glu Glu Gly Ser Phe His
390                 395                 400 cca ctg ggc atg tcc ggg gca ggg agc tgaaaggact ccaccgctgc           1303
Pro Leu Gly Met Ser Gly Ala Gly Ser
    405                 410 cctcctggaa ctgctgtact gggtccagaa gcctctcagc caggagggag ctggccctgg   1363
aagggacctg agctggggga cactggctcc tgccatctcc tctgccatga agatacacca   1423
ttgagacttg actgggcaac accagcgtcc cccacccgcg tcgtggtgta gtcatagagc   1483
tgcaagctga gctggcgagg ggatggttgt tgacccctct ctcctagaga ccttgaggct   1543
ggcacggcga ctcccaactc agcctgctct cactacgagt tttcatactc tgcctccccc   1603
attgggaggg cccattccc                                                1622

<210> SEQ ID NO 8
<211> LENGTH: 1190
<212> TYPE: DNA
<213> ORGANISM: Homo sapiens
<220> FEATURE:
<221> NAME/KEY: CDS
<222> LOCATION: (1)..(1188)

<400> SEQUENCE: 8 atg gct ctc ctg acc aat cta ctg ccc ttg tgc tgc ttg gca ctt ctg       48
Met Ala Leu Leu Thr Asn Leu Leu Pro Leu Cys Cys Leu Ala Leu Leu
1               5                   10                  15 gcg ctg cca gcc cag agc tgc ggg ccg ggc cgg ggg ccg gtt ggc cgg       96
Ala Leu Pro Ala Gln Ser Cys Gly Pro Gly Arg Gly Pro Val Gly Arg
                20                  25                  30 cgc cgc tat gcg cgc aag cag ctc gtg ccg cta ctc tac aag caa ttt      144
Arg Arg Tyr Ala Arg Lys Gln Leu Val Pro Leu Leu Tyr Lys Gln Phe
            35                  40                  45 gtg ccc ggc gtg cca gag cgg acc ctg ggc gcc agt ggg cca gcg gag      192
Val Pro Gly Val Pro Glu Arg Thr Leu Gly Ala Ser Gly Pro Ala Glu
        50                  55                  60
```

|  |  |
|---|---|
| ggg agg gtg gca agg ggc tcc gag cgc ttc cgg gac ctc gtg ccc aac<br>Gly Arg Val Ala Arg Gly Ser Glu Arg Phe Arg Asp Leu Val Pro Asn<br>65                            70                       75                      80 | 240 |
| tac aac ccc gac atc atc ttc aag gat gag gag aac agt gga gcc gac<br>Tyr Asn Pro Asp Ile Ile Phe Lys Asp Glu Glu Asn Ser Gly Ala Asp<br>                       85                       90                       95 | 288 |
| cgc ctg atg acc gag cgt tgc aag gag agg gtg aac gct ttg gcc att<br>Arg Leu Met Thr Glu Arg Cys Lys Glu Arg Val Asn Ala Leu Ala Ile<br>             100                   105                  110 | 336 |
| gcc gtg atg aac atg tgg ccc gga gtg cgc cta cga gtg act gag ggc<br>Ala Val Met Asn Met Trp Pro Gly Val Arg Leu Arg Val Thr Glu Gly<br>             115                   120                  125 | 384 |
| tgg gac gag gac ggc cac cac gct cag gat tca ctc cac tac gaa ggc<br>Trp Asp Glu Asp Gly His His Ala Gln Asp Ser Leu His Tyr Glu Gly<br>130                           135                   140 | 432 |
| cgt gct ttg gac atc act acg tct gac cgc gac cgc aac aag tat ggg<br>Arg Ala Leu Asp Ile Thr Thr Ser Asp Arg Asp Arg Asn Lys Tyr Gly<br>145                        150                   155                  160 | 480 |
| ttg ctg gcg cgc ctc gca gtg gaa gcc ggc ttc gac tgg gtc tac tac<br>Leu Leu Ala Arg Leu Ala Val Glu Ala Gly Phe Asp Trp Val Tyr Tyr<br>                     165                   170                  175 | 528 |
| gag tcc cgc aac cac gtc cac gtg tcg gtc aaa gct gat aac tca ctg<br>Glu Ser Arg Asn His Val His Val Ser Val Lys Ala Asp Asn Ser Leu<br>             180                   185                  190 | 576 |
| gcg gtc cgg gcg ggc ggc tgc ttt ccg gga aat gca act gtg cgc ctg<br>Ala Val Arg Ala Gly Gly Cys Phe Pro Gly Asn Ala Thr Val Arg Leu<br>             195                   200                  205 | 624 |
| tgg agc ggc gag cgg aaa ggc ctg cgg gaa ctg cac cgc gga gac tgg<br>Trp Ser Gly Glu Arg Lys Gly Leu Arg Glu Leu His Arg Gly Asp Trp<br>210                           215                   220 | 672 |
| gtt ttg gcg gcc gat gcg tca ggc cgg gtg gtg ccc acg ccg gtg ctg<br>Val Leu Ala Ala Asp Ala Ser Gly Arg Val Val Pro Thr Pro Val Leu<br>225                        230                   235                  240 | 720 |
| ctc ttc ctg gac cgg gac ttg cag cgc cgg gct tca ttt gtg gct gtg<br>Leu Phe Leu Asp Arg Asp Leu Gln Arg Arg Ala Ser Phe Val Ala Val<br>                     245                   250                  255 | 768 |
| gag acc gag tgg cct cca cgc aaa ctg ttg ctc acg ccc tgg cac ctg<br>Glu Thr Glu Trp Pro Pro Arg Lys Leu Leu Thr Pro Trp His Leu<br>                   260                   265                  270 | 816 |
| gtg ttt gcc gct cga ggg ccg gcg ccc gcg cca ggc gac ttt gca ccg<br>Val Phe Ala Ala Arg Gly Pro Ala Pro Ala Pro Gly Asp Phe Ala Pro<br>             275                   280                  285 | 864 |
| gtg ttc gcg cgc cgg cta cgc gct ggg gac tcg gtg ctg gcg ccc ggc<br>Val Phe Ala Arg Arg Leu Arg Ala Gly Asp Ser Val Leu Ala Pro Gly<br>             290                   295                  300 | 912 |
| ggg gat gcg ctt cgg cca gcg cgc gtg gcc cgt gtg gcg cgg gag gaa<br>Gly Asp Ala Leu Arg Pro Ala Arg Val Ala Arg Val Ala Arg Glu Glu<br>305                           310                   315                  320 | 960 |
| gcc gtg ggc gtg ttc gcg ccg ctc acc gcg cac ggg acg ctg ctg gtg<br>Ala Val Gly Val Phe Ala Pro Leu Thr Ala His Gly Thr Leu Leu Val<br>                     325                   330                  335 | 1008 |
| aac gat gtc ctg gcc tct tgc tac gcg gtt ctg gag agt cac cag tgg<br>Asn Asp Val Leu Ala Ser Cys Tyr Ala Val Leu Glu Ser His Gln Trp<br>             340                   345                  350 | 1056 |
| gcg cac cgc gct ttt gcc ccc ttg aga ctg ctg cac gcg cta ggg gcg<br>Ala His Arg Ala Phe Ala Pro Leu Arg Leu Leu His Ala Leu Gly Ala<br>             355                   360                  365 | 1104 |
| ctg ctc ccc ggc ggg gcc gtc cag ccg act ggc atg cat tgg tac tct<br>Leu Leu Pro Gly Gly Ala Val Gln Pro Thr Gly Met His Trp Tyr Ser<br>370                           375                   380 | 1152 |

-continued

```
cgg ctc ctc tac cgc tta gcg gag gag cta ctg ggc tg                    1190
Arg Leu Leu Tyr Arg Leu Ala Glu Glu Leu Leu Gly
385                 390                 395

<210> SEQ ID NO 9
<211> LENGTH: 1251
<212> TYPE: DNA
<213> ORGANISM: Brachydanio rerio
<220> FEATURE:
<221> NAME/KEY: CDS
<222> LOCATION: (1)..(1248)

<400> SEQUENCE: 9 atg gac gta agg ctg cat ctg aag caa ttt gct tta ctg tgt ttt atc        48
Met Asp Val Arg Leu His Leu Lys Gln Phe Ala Leu Leu Cys Phe Ile
 1               5                  10                  15 agc ttg ctt ctg acg cct tgt gga tta gcc tgt ggt cct ggt aga ggt        96
Ser Leu Leu Leu Thr Pro Cys Gly Leu Ala Cys Gly Pro Gly Arg Gly
             20                  25                  30 tat gga aaa cga aga cac cca aag aaa tta acc ccg ttg gct tac aag       144
Tyr Gly Lys Arg Arg His Pro Lys Lys Leu Thr Pro Leu Ala Tyr Lys
         35                  40                  45 caa ttc atc ccc aac gtt gct gag aaa acg ctt gga gcc agc ggc aaa       192
Gln Phe Ile Pro Asn Val Ala Glu Lys Thr Leu Gly Ala Ser Gly Lys
     50                  55                  60 tac gaa ggc aaa atc aca agg aat tca gag aga ttt aaa gag ctg att       240
Tyr Glu Gly Lys Ile Thr Arg Asn Ser Glu Arg Phe Lys Glu Leu Ile
 65                  70                  75                  80 ccg aat tat aat ccc gat atc atc ttt aag gac gag gaa aac aca aac       288
Pro Asn Tyr Asn Pro Asp Ile Ile Phe Lys Asp Glu Glu Asn Thr Asn
                 85                  90                  95 gct gac agg ctg atg acc aag cgc tgt aag gac aag tta aat tcg ttg       336
Ala Asp Arg Leu Met Thr Lys Arg Cys Lys Asp Lys Leu Asn Ser Leu
            100                 105                 110 gcc ata tcc gtc atg aac cac tgg ccc ggc gtg aaa ctg cgc gtc act       384
Ala Ile Ser Val Met Asn His Trp Pro Gly Val Lys Leu Arg Val Thr
        115                 120                 125 gaa ggc tgg gat gag gat ggt cac cat tta gaa gaa tct ttg cac tat       432
Glu Gly Trp Asp Glu Asp Gly His His Leu Glu Glu Ser Leu His Tyr
    130                 135                 140 gag gga cgg gca gtg gac atc act acc tca gac agg gat aaa agc aag       480
Glu Gly Arg Ala Val Asp Ile Thr Thr Ser Asp Arg Asp Lys Ser Lys
145                 150                 155                 160 tat ggg atg cta tcc agg ctt gca gtg gag gca gga ttc gac tgg gtc       528
Tyr Gly Met Leu Ser Arg Leu Ala Val Glu Ala Gly Phe Asp Trp Val
                165                 170                 175 tat tat gaa tct aaa gcc cac ata cac tgc tct gtc aaa gca gaa aat       576
Tyr Tyr Glu Ser Lys Ala His Ile His Cys Ser Val Lys Ala Glu Asn
            180                 185                 190 tca gtg gct gct aaa tca gga gga tgt ttt cct ggg tct ggg acg gtg       624
Ser Val Ala Ala Lys Ser Gly Gly Cys Phe Pro Gly Ser Gly Thr Val
        195                 200                 205 aca ctt ggt gat ggg acg agg aaa ccc atc aaa gat ctt aaa gtg ggc       672
Thr Leu Gly Asp Gly Thr Arg Lys Pro Ile Lys Asp Leu Lys Val Gly
    210                 215                 220 gac cgg gtt ttg gct gca gac gag aag gga aat gtc tta ata agc gac       720
Asp Arg Val Leu Ala Ala Asp Glu Lys Gly Asn Val Leu Ile Ser Asp
225                 230                 235                 240 ttt att atg ttt ata gac cac gat ccg aca acg aga agg caa ttc atc       768
Phe Ile Met Phe Ile Asp His Asp Pro Thr Thr Arg Arg Gln Phe Ile
                245                 250                 255
```

```
gtc atc gag acg tca gaa cct ttc acc aag ctc acc ctc act gcc gcg      816
Val Ile Glu Thr Ser Glu Pro Phe Thr Lys Leu Thr Leu Thr Ala Ala
            260                 265                 270 cac cta gtt ttc gtt gga aac tct tca gca gct tcg ggt ata aca gca      864
His Leu Val Phe Val Gly Asn Ser Ser Ala Ala Ser Gly Ile Thr Ala
        275                 280                 285 aca ttt gcc agc aac gtg aag cct gga gat aca gtt tta gtg tgg gaa      912
Thr Phe Ala Ser Asn Val Lys Pro Gly Asp Thr Val Leu Val Trp Glu
    290                 295                 300 gac aca tgc gag agc ctc aag agc gtt aca gtg aaa agg att tac act      960
Asp Thr Cys Glu Ser Leu Lys Ser Val Thr Val Lys Arg Ile Tyr Thr
305                 310                 315                 320 gag gag cac gag ggc tct ttt gcg cca gtc acc gcg cac gga acc ata     1008
Glu Glu His Glu Gly Ser Phe Ala Pro Val Thr Ala His Gly Thr Ile
                325                 330                 335 ata gtg gat cag gtg ttg gca tcg tgc tac gcg gtc att gag aac cac     1056
Ile Val Asp Gln Val Leu Ala Ser Cys Tyr Ala Val Ile Glu Asn His
            340                 345                 350 aaa tgg gca cat tgg gct ttt gcg ccg gtc agg ttg tgt cac aag ctg     1104
Lys Trp Ala His Trp Ala Phe Ala Pro Val Arg Leu Cys His Lys Leu
        355                 360                 365 atg acg tgg ctt ttt ccg gct cgt gaa tca aac gtc aat ttt cag gag     1152
Met Thr Trp Leu Phe Pro Ala Arg Glu Ser Asn Val Asn Phe Gln Glu
    370                 375                 380 gat ggt atc cac tgg tac tca aat atg ctg ttt cac atc ggc tct tgg     1200
Asp Gly Ile His Trp Tyr Ser Asn Met Leu Phe His Ile Gly Ser Trp
385                 390                 395                 400 ctg ctg gac aga gac tct ttc cat cca ctc ggg att tta cac tta agt     1248
Leu Leu Asp Arg Asp Ser Phe His Pro Leu Gly Ile Leu His Leu Ser
                405                 410                 415 tga                                                                 1251

<210> SEQ ID NO 10
<211> LENGTH: 425
<212> TYPE: PRT
<213> ORGANISM: Gallus sp.

<400> SEQUENCE: 10

Met Val Glu Met Leu Leu Leu Thr Arg Ile Leu Leu Val Gly Phe Ile
 1               5                  10                  15

Cys Ala Leu Leu Val Ser Ser Gly Leu Thr Cys Gly Pro Gly Arg Gly
            20                  25                  30

Ile Gly Lys Arg Arg His Pro Lys Lys Leu Thr Pro Leu Ala Tyr Lys
        35                  40                  45

Gln Phe Ile Pro Asn Val Ala Glu Lys Thr Leu Gly Ala Ser Gly Arg
    50                  55                  60

Tyr Glu Gly Lys Ile Thr Arg Asn Ser Glu Arg Phe Lys Glu Leu Thr
65                  70                  75                  80

Pro Asn Tyr Asn Pro Asp Ile Ile Phe Lys Asp Glu Glu Asn Thr Gly
                85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
    130                 135                 140

Glu Gly Arg Ala Val Asp Ile Thr Thr Ser Asp Arg Asp Arg Ser Lys
```

```
                145                 150                 155                 160
Tyr Gly Met Leu Ala Arg Leu Ala Val Glu Ala Gly Phe Asp Trp Val
                165                 170                 175
Tyr Tyr Glu Ser Lys Ala His Ile His Cys Ser Val Lys Ala Glu Asn
                180                 185                 190
Ser Val Ala Ala Lys Ser Gly Gly Cys Phe Pro Gly Ser Ala Thr Val
                195                 200                 205
His Leu Glu His Gly Gly Thr Lys Leu Val Lys Asp Leu Ser Pro Gly
            210                 215                 220
Asp Arg Val Leu Ala Ala Asp Ala Asp Gly Arg Leu Leu Tyr Ser Asp
225                 230                 235                 240
Phe Leu Thr Phe Leu Asp Arg Met Asp Ser Ser Arg Lys Leu Phe Tyr
                245                 250                 255
Val Ile Glu Thr Arg Gln Pro Arg Ala Arg Leu Leu Thr Ala Ala
                260                 265                 270
His Leu Leu Phe Val Ala Pro Gln His Asn Gln Ser Glu Ala Thr Gly
            275                 280                 285
Ser Thr Ser Gly Gln Ala Leu Phe Ala Ser Asn Val Lys Pro Gly Gln
        290                 295                 300
Arg Val Tyr Val Leu Gly Glu Gly Gln Gln Leu Leu Pro Ala Ser
305                 310                 315                 320
Val His Ser Val Ser Leu Arg Glu Glu Ala Ser Gly Ala Tyr Ala Pro
                325                 330                 335
Leu Thr Ala Gln Gly Thr Ile Leu Ile Asn Arg Val Leu Ala Ser Cys
                340                 345                 350
Tyr Ala Val Ile Glu Glu His Ser Trp Ala His Trp Ala Phe Ala Pro
                355                 360                 365
Phe Arg Leu Ala Gln Gly Leu Leu Ala Ala Leu Cys Pro Asp Gly Ala
            370                 375                 380
Ile Pro Thr Ala Ala Thr Thr Thr Gly Ile His Trp Tyr Ser Arg
385                 390                 395                 400
Leu Leu Tyr Arg Ile Gly Ser Trp Val Leu Asp Gly Asp Ala Leu His
                405                 410                 415
Pro Leu Gly Met Val Ala Pro Ser
            420                 425

<210> SEQ ID NO 11
<211> LENGTH: 396
<212> TYPE: PRT
<213> ORGANISM: Murine sp.

<400> SEQUENCE: 11

Met Ala Leu Pro Ala Ser Leu Leu Pro Leu Cys Cys Leu Ala Leu Leu
1               5                   10                  15
Ala Leu Ser Ala Gln Ser Cys Gly Pro Gly Arg Gly Pro Val Gly Arg
                20                  25                  30
Arg Arg Tyr Val Arg Lys Gln Leu Val Pro Leu Leu Tyr Lys Gln Phe
            35                  40                  45
Val Pro Ser Met Pro Glu Arg Thr Leu Gly Ala Ser Gly Pro Ala Glu
        50                  55                  60
Gly Arg Val Thr Arg Gly Ser Glu Arg Phe Arg Asp Leu Val Pro Asn
65                  70                  75                  80
Tyr Asn Pro Asp Ile Ile Phe Lys Asp Glu Glu Asn Ser Gly Ala Asp
                85                  90                  95
```

```
Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: Murine sp.

<400> SEQUENCE: 12

Met Ser Pro Ala Trp Leu Arg Pro Arg Leu Arg Phe Cys Leu Phe Leu
1               5                   10                  15

Leu Leu Leu Leu Leu Val Pro Ala Ala Arg Gly Cys Gly Pro Gly Arg
                20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80
```

```
Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Asn Gly Glu Arg Val Ala Leu Ser Ala Val Lys
    210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285

His Phe Arg Ala Thr Phe Ala Ser His Val Gln Pro Gly Gln Tyr Val
    290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Ser Tyr
    370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410

<210> SEQ ID NO 13
<211> LENGTH: 437
<212> TYPE: PRT
<213> ORGANISM: Murine sp.

<400> SEQUENCE: 13

Met Leu Leu Leu Leu Ala Arg Cys Phe Leu Val Ile Leu Ala Ser Ser
  1               5                  10                  15

Leu Leu Val Cys Pro Gly Leu Ala Cys Gly Pro Gly Arg Gly Phe Gly
             20                  25                  30

Lys Arg Arg His Pro Lys Lys Leu Thr Pro Leu Ala Tyr Lys Gln Phe
```

```
            35                  40                  45
Ile Pro Asn Val Ala Glu Lys Thr Leu Gly Ala Ser Gly Arg Tyr Glu
             50                  55                  60

Gly Lys Ile Thr Arg Asn Ser Glu Arg Phe Lys Glu Leu Thr Pro Asn
 65                  70                  75                  80

Tyr Asn Pro Asp Ile Ile Phe Lys Asp Glu Asn Thr Gly Ala Asp
                     85                  90                  95

Arg Leu Met Thr Gln Arg Cys Lys Asp Lys Leu Asn Ala Leu Ala Ile
                100                 105                 110

Ser Val Met Asn Gln Trp Pro Gly Val Arg Leu Arg Val Thr Glu Gly
            115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
                180                 185                 190

Ala Ala Lys Ser Gly Gly Cys Phe Pro Gly Ser Ala Thr Val His Leu
            195                 200                 205

Glu Gln Gly Gly Thr Lys Leu Val Lys Asp Leu Arg Pro Gly Asp Arg
210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
                260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
            370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 14
```

<211> LENGTH: 418
<212> TYPE: PRT
<213> ORGANISM: Brachydanio rerio

<400> SEQUENCE: 14

```
Met Arg Leu Leu Thr Arg Val Leu Leu Val Ser Leu Leu Thr Leu Ser
 1               5                  10                  15

Leu Val Val Ser Gly Leu Ala Cys Gly Pro Gly Arg Gly Tyr Gly Arg
             20                  25                  30

Arg Arg His Pro Lys Lys Leu Thr Pro Leu Ala Tyr Lys Gln Phe Ile
         35                  40                  45

Pro Asn Val Ala Glu Lys Thr Leu Gly Ala Ser Gly Arg Tyr Glu Gly
     50                  55                  60

Lys Ile Thr Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Val Ser Ser
        355                 360                 365

Phe Leu Ser Pro Lys Thr Pro Ala Val Gly Pro Met Arg Leu Tyr Asn
    370                 375                 380

Arg Arg Gly Ser Thr Gly Thr Pro Gly Ser Cys His Gln Met Gly Thr
```

-continued

```
                385                 390                 395                 400
Trp Leu Leu Asp Ser Asn Met Leu His Pro Leu Gly Met Ser Val Asn
                405                 410                 415
Ser Ser

<210> SEQ ID NO 15
<211> LENGTH: 475
<212> TYPE: PRT
<213> ORGANISM: Homo sapiens
<220> FEATURE:
<223> OTHER INFORMATION: Xaa at position 463 is any or unknown amino
      acid

<400> SEQUENCE: 15

Met Leu Leu Leu Ala Arg Cys Leu Leu Leu Val Leu Val Ser Ser Leu
  1               5                  10                  15

Leu Val Cys Ser Gly Leu Ala Cys Gly Pro Gly Arg Gly Phe Gly Lys
                 20                  25                  30

Arg Arg His Pro Lys Lys Leu Thr Pro Leu Ala Tyr Lys Gln Phe Ile
             35                  40                  45

Pro Asn Val Ala Glu Lys Thr Leu Gly Ala Ser Gly Arg Tyr Glu Gly
 50                  55                  60

Lys Ile Ser Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
            115                 120                 125

Asp Glu Asp Gly His His Ser Glu Gly Ser Leu His Tyr Glu Gly Arg
130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
            195                 200                 205

Gln Gly Gly Thr Lys Leu Val Lys Asp Leu Ser Pro Gly Asp Arg Val
        210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
        290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
```

-continued

```
                325                 330                 335
Leu Ser Glu Glu Ala Ala Gly Ala Tyr Ala Pro Leu Thr Ala Gln Gly
            340                 345                 350
Thr Ile Leu Ile Asn Arg Val Leu Ala Ser Cys Tyr Ala Val Ile Glu
            355                 360                 365
Glu His Ser Trp Ala His Arg Ala Phe Ala Pro Phe Arg Leu Ala His
            370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Gly Arg Val Ala Leu Thr
            405                 410                 415
Ala Pro Gly Ala Ala Asp Ala Pro Gly Ala Gly Ala Thr Ala Gly Ile
            420                 425                 430
His Trp Tyr Ser Gln Leu Leu Tyr Gln Ile Gly Thr Trp Leu Leu Asp
            435                 440                 445
Ser Glu Ala Leu His Pro Leu Gly Met Ala Val Lys Ser Ser Xaa Ser
            450                 455                 460
Arg Gly Ala Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
1               5                   10                  15
Leu Leu Leu Leu Val Val Pro Ala Ala Trp Gly Cys Gly Pro Gly Arg
                20                  25                  30
Val Val Gly Ser Arg Arg Arg Pro Pro Arg Lys Leu Val Pro Leu Ala
            35                  40                  45
Tyr Lys Gln Phe Ser Pro Asn Val Pro Glu Lys Thr Leu Gly Ala Ser
        50                  55                  60
Gly Arg Tyr Glu Gly Lys Ile Ala Arg Ser Ser Glu Arg Phe Lys Glu
65                  70                  75                  80
Leu Thr Pro Asn Tyr Asn Pro Asp Ile Ile Phe Lys Asp Glu Glu Asn
                85                  90                  95
Thr Gly Ala Asp Arg Leu Met Thr Gln Arg Cys Lys Asp Arg Leu Asn
            100                 105                 110
Ser Leu Ala Ile Ser Val Met Asn Gln Trp Pro Gly Val Lys Leu Arg
        115                 120                 125
Val Thr Glu Gly Trp Asp Glu Asp Gly His His Ser Glu Glu Ser Leu
130                 135                 140
His Tyr Glu Gly Arg Ala Val Asp Ile Thr Thr Ser Asp Arg Asp Arg
145                 150                 155                 160
Asn Lys Tyr Gly Leu Leu Ala Arg Leu Ala Val Glu Ala Gly Phe Asp
                165                 170                 175
Trp Val Tyr Tyr Glu Ser Lys Ala His Val His Cys Ser Val Lys Ser
            180                 185                 190
Glu His Ser Ala Ala Ala Lys Thr Gly Gly Cys Phe Pro Ala Gly Ala
        195                 200                 205
Gln Val Arg Leu Glu Ser Gly Ala Arg Val Ala Leu Ser Ala Val Arg
210                 215                 220
```

-continued

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
            245                 250                 255

Phe Gln Val Ile Glu Thr Gln Asp Pro Pro Arg Arg Leu Ala Leu Thr
        260                 265                 270

Pro Ala His Leu Leu Phe Thr Ala Asp Asn His Thr Glu Pro Ala Ala
    275                 280                 285

Arg Phe Arg Ala Thr Phe Ala Ser His Val Gln Pro Gly Gln Tyr Val
290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
            325                 330                 335

Thr Leu Val Val Glu Asp Val Val Ala Ser Cys Phe Ala Ala Val Ala
        340                 345                 350

Asp His His Leu Ala Gln Leu Ala Phe Trp Pro Leu Arg Leu Phe His
    355                 360                 365

Ser Leu Ala Trp Gly Ser Trp Thr Pro Gly Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410

<210> SEQ ID NO 17
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
1               5                   10                  15

Ala Leu Pro Ala Gln Ser Cys Gly Pro Gly Arg Gly Pro Val Gly Arg
            20                  25                  30

Arg Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

```
Ala Val Arg Ala Gly Gly Cys Phe Pro Gly Asn Ala Thr Val Arg Leu
            195                 200                 205

Trp Ser Gly Glu Arg Lys Gly Leu Arg Glu Leu His Arg Gly Asp Trp
210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
            245                 250                 255

Glu Thr Glu Trp Pro Pro Arg Lys Leu Leu Thr Pro Trp His Leu
            260                 265                 270

Val Phe Ala Ala Arg Gly Pro Ala Pro Ala Pro Gly Asp Phe Ala Pro
            275                 280                 285

Val Phe Ala Arg Arg Leu Arg Ala Gly Asp Ser Val Leu Ala Pro Gly
            290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
            325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
            355                 360                 365

Leu Leu Pro Gly Gly Ala Val Gln Pro Thr Gly Met His Trp Tyr Ser
            370                 375                 380

Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Brachydanio rerio

<400> SEQUENCE: 18

Met Asp Val Arg Leu His Leu Lys Gln Phe Ala Leu Leu Cys Phe Ile
1               5                   10                  15

Ser Leu Leu Leu Thr Pro Cys Gly Leu Ala Cys Gly Pro Gly Arg Gly
            20                  25                  30

Tyr Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Lys
    50                  55                  60

Tyr Glu Gly Lys Ile Thr Arg Asn Ser Glu Arg Phe Lys Glu Leu Ile
65                  70                  75                  80

Pro Asn Tyr Asn Pro Asp Ile Ile Phe Lys Asp Glu Glu Asn Thr
                85                  90                  95

Ala Asp Arg Leu Met Thr Lys Arg Cys Lys Asp Lys Leu Asn Ser Leu
            100                 105                 110

Ala Ile Ser Val Met Asn His Trp Pro Gly Val Lys Leu Arg Val Thr
            115                 120                 125

Glu Gly Trp Asp Glu Asp Gly His His Leu Glu Glu Ser Leu His Tyr
        130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
```

```
              165                 170                 175
Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Gly Thr Val
            195                 200                 205

Thr Leu Gly Asp Gly Thr Arg Lys Pro Ile Lys Asp Leu Lys Val Gly
            210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
            260                 265                 270

His Leu Val Phe Val Gly Asn Ser Ala Ala Ser Gly Ile Thr Ala
            275                 280                 285

Thr Phe Ala Ser Asn Val Lys Pro Gly Asp Thr Val Leu Val Trp Glu
            290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
                340                 345                 350

Lys Trp Ala His Trp Ala Phe Ala Pro Val Arg Leu Cys His Lys Leu
            355                 360                 365

Met Thr Trp Leu Phe Pro Ala Arg Glu Ser Asn Val Asn Phe Gln Glu
370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
            405                 410                 415

<210> SEQ ID NO 19
<211> LENGTH: 1416
<212> TYPE: DNA
<213> ORGANISM: Drosophila sp.
<220> FEATURE:
<221> NAME/KEY: CDS
<222> LOCATION: (1)..(1413)

<400> SEQUENCE: 19 atg gat aac cac agc tca gtg cct tgg gcc agt gcc gcc agt gtc acc      48
Met Asp Asn His Ser Ser Val Pro Trp Ala Ser Ala Ala Ser Val Thr
 1               5                  10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
                20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
            35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
    50                  55                  60 acc tct ctg gtg gcc ctg ctg ctg atc gtc ttg ccg atg gtc ttt agc     240
Thr Ser Leu Val Ala Leu Leu Leu Ile Val Leu Pro Met Val Phe Ser
65                  70                  75                  80 ccg gct cac agc tgc ggt cct ggc cga gga ttg ggt cgt cat agg gcg     288
```

```
              Pro Ala His Ser Cys Gly Pro Gly Arg Gly Leu Gly Arg His Arg Ala
                          85                  90                  95 cgc aac ctg tat ccg ctg gtc ctc aag cag aca att ccc aat cta tcc        336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg        384
Glu Tyr Thr Asn Ser Ala Ser Gly Pro Leu Glu Gly Val Ile Arg Arg
            115                 120                 125 gat tcg ccc aaa ttc aag gac ctc gtg ccc aac tac aac agg gac atc        432
Asp Ser Pro Lys Phe Lys Asp Leu Val Pro Asn Tyr Asn Arg Asp Ile
        130                 135                 140 ctt ttc cgt gac gag gaa ggc acc gga gcg gat ggc ttg atg agc aag        480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa        528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac        576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att        624
His His Gly Gln Glu Ser Leu His Tyr Glu Gly Arg Ala Val Thr Ile
            195                 200                 205 gcc acc tcc gat cgc gac cag tcc aaa tac ggc atg ctc gct cgc ctg        672
Ala Thr Ser Asp Arg Asp Gln Ser Lys Tyr Gly Met Leu Ala Arg Leu
        210                 215                 220 gcc gtc gag gct gga ttc gat tgg gtc tcc tac gtc agc agg cgc cac        720
Ala Val Glu Ala Gly Phe Asp Trp Val Ser Tyr Val Ser Arg Arg His
225                 230                 235                 240 atc tac tgc tcc gtc aag tca gat tcg tcg atc agt tcc cac gtg cac        768
Ile Tyr Cys Ser Val Lys Ser Asp Ser Ser Ile Ser Ser His Val His
                245                 250                 255 ggc tgc ttc acg ccg gag agc aca gcg ctg ctg gag agt gga gtc cgg        816
Gly Cys Phe Thr Pro Glu Ser Thr Ala Leu Leu Glu Ser Gly Val Arg
            260                 265                 270 aag ccg ctc ggc gag ctc tct atc gga gat cgt gtt ttg agc atg acc        864
Lys Pro Leu Gly Glu Leu Ser Ile Gly Asp Arg Val Leu Ser Met Thr
            275                 280                 285 gcc aac gga cag gcc gtc tac agc gaa gtg atc ctc ttc atg gac cgc        912
Ala Asn Gly Gln Ala Val Tyr Ser Glu Val Ile Leu Phe Met Asp Arg
        290                 295                 300 aac ctc gag cag atg caa aac ttt gtg cag ctg cac acg gac ggt gga        960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg       1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag       1056
Glu Ser Gln Lys Leu Thr Phe Val Phe Ala His Arg Ile Glu Glu Lys
            340                 345                 350 aac cag gtg ctc gta cgg gat gtg gag acg ggc gag ctg agg ccc cag       1104
Asn Gln Val Leu Val Arg Asp Val Glu Thr Gly Glu Leu Arg Pro Gln
            355                 360                 365 cga gtg gtc aag ttg ggc agt gtg cgc agt aag ggc gtg gtc gcg ccg       1152
Arg Val Val Lys Leu Gly Ser Val Arg Ser Lys Gly Val Val Ala Pro
        370                 375                 380 ctg acc cgc gag ggc acc att gtg gtc aac tcg gtg gcc gcc agt tgc       1200
Leu Thr Arg Glu Gly Thr Ile Val Val Asn Ser Val Ala Ala Ser Cys
385                 390                 395                 400
```

-continued

```
tat gcg gtg atc aac agt cag tcg ctg gcc cac tgg gga ctg gct ccc      1248
Tyr Ala Val Ile Asn Ser Gln Ser Leu Ala His Trp Gly Leu Ala Pro
            405                 410                 415 atg cgc ctg ctg tcc acg ctg gag gcg tgg ctg ccc gcc aag gag cag      1296
Met Arg Leu Leu Ser Thr Leu Glu Ala Trp Leu Pro Ala Lys Glu Gln
        420                 425                 430 ttg cac agt tcg ccg aag gtg gtg agc tcg gcg cag cag cag aat ggc      1344
Leu His Ser Ser Pro Lys Val Val Ser Ser Ala Gln Gln Gln Asn Gly
    435                 440                 445 atc cat tgg tat gcc aat gcg ctc tac aag gtc aag gac tac gtg ctg      1392
Ile His Trp Tyr Ala Asn Ala Leu Tyr Lys Val Lys Asp Tyr Val Leu
450                 455                 460 ccg cag agc tgg cgc cac gat tga                                      1416
Pro Gln Ser Trp Arg His Asp
465                 470

<210> SEQ ID NO 20
<211> LENGTH: 471
<212> TYPE: PRT
<213> ORGANISM: Drosophila sp.

<400> SEQUENCE: 20

Met Asp Asn His Ser Ser Val Pro Trp Ala Ser Ala Ser Val Thr
1               5                   10                  15

Cys Leu Ser Leu Gly Cys Gln Met Pro Gln Phe Gln Phe Gln Phe Gln
            20                  25                  30

Leu Gln Ile Arg Ser Glu Leu His Leu Arg Lys Pro Ala Arg Arg Thr
        35                  40                  45

Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
            100                 105                 110

Glu Tyr Thr Asn Ser Ala Ser Gly Pro Leu Glu Gly Val Ile Arg Arg
        115                 120                 125

Asp Ser Pro Lys Phe Lys Asp Leu Val Pro Asn Tyr Asn Arg Asp Ile
    130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270
```

```
Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
    290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
                340                 345                 350

Asn Gln Val Leu Val Arg Asp Val Glu Thr Gly Glu Leu Arg Pro Gln
            355                 360                 365

Arg Val Val Lys Leu Gly Ser Val Arg Ser Lys Gly Val Val Ala Pro
    370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ser Ala Gln Gln Asn Gly
                435                 440                 445

Ile His Trp Tyr Ala Asn Ala Leu Tyr Lys Val Lys Asp Tyr Val Leu
    450                 455                 460

Pro Gln Ser Trp Arg His Asp
465                 470

<210> SEQ ID NO 21
<211> LENGTH: 221
<212> TYPE: PRT
<213> ORGANISM: Artificial Sequence
<220> FEATURE:
<223> OTHER INFORMATION: Description of Artificial Sequence: degenerate
      polypeptide sequence
<220> FEATURE:
<221> NAME/KEY: MOD_RES
<222> LOCATION: (7)
<223> OTHER INFORMATION: Gly, Ala, Val, Leu, Ile, Phe, Tyr or Trp
<220> FEATURE:
<221> NAME/KEY: MOD_RES
<222> LOCATION: (9)
<223> OTHER INFORMATION: Arg, His or Lys
<220> FEATURE:
<221> NAME/KEY: MOD_RES
<222> LOCATION: (44)
<223> OTHER INFORMATION: Gly, Ala, Val, Leu, Ile, Ser or Thr
<220> FEATURE:
<221> NAME/KEY: MOD_RES
<222> LOCATION: (85)
<223> OTHER INFORMATION: Gly, Ala, Val, Leu, Ile, Ser or Thr
<220> FEATURE:
<221> NAME/KEY: MOD_RES
<222> LOCATION: (93)
<223> OTHER INFORMATION: Lys, Arg, His, Asn or Gln
<220> FEATURE:
<221> NAME/KEY: MOD_RES
<222> LOCATION: (98)
<223> OTHER INFORMATION: Lys, Arg or His
<220> FEATURE:
<221> NAME/KEY: MOD_RES
<222> LOCATION: (112)
<223> OTHER INFORMATION: Ser, Thr, Tyr, Trp or Phe
<220> FEATURE:
<221> NAME/KEY: MOD_RES
<222> LOCATION: (132)
<223> OTHER INFORMATION: Lys, Arg or His
```

```
<220> FEATURE:
<221> NAME/KEY: MOD_RES
<222> LOCATION: (137)
<223> OTHER INFORMATION: Met, Cys, Ser or Thr
<220> FEATURE:
<221> NAME/KEY: MOD_RES
<222> LOCATION: (139)
<223> OTHER INFORMATION: Gly, Ala, Val, Leu, Ile, Ser or Thr
<220> FEATURE:
<221> NAME/KEY: MOD_RES
<222> LOCATION: (181)
<223> OTHER INFORMATION: Leu, Val, Met, Thr or Ser
<220> FEATURE:
<221> NAME/KEY: MOD_RES
<222> LOCATION: (183)
<223> OTHER INFORMATION: His, Phe, Tyr, Ser, Thr, Met or Cys
<220> FEATURE:
<221> NAME/KEY: MOD_RES
<222> LOCATION: (185)
<223> OTHER INFORMATION: Gln, Asn, Glu, or Asp
<220> FEATURE:
<221> NAME/KEY: MOD_RES
<222> LOCATION: (186)
<223> OTHER INFORMATION: His, Phe, Tyr, Thr, Gln, Asn, Glu or Asp
<220> FEATURE:
<221> NAME/KEY: MOD-RES
<222> LOCATION: (189)
<223> OTHER INFORMATION: Gln, Asn, Glu, Asp, Thr, Ser, Met or Cys
<220> FEATURE:
<221> NAME/KEY: MOD_RES
<222> LOCATION: (191)
<223> OTHER INFORMATION: Ala, Gly, Cys, Leu, Val or Met
<220> FEATURE:
<221> NAME/KEY: MOD_RES
<222> LOCATION: (196)
<223> OTHER INFORMATION: Arg, Lys, Met, Ile, Asn, Asp, Glu, Gln, Ser,
      Thr or Cys
<220> FEATURE:
<221> NAME/KEY: MOD_RES
<222> LOCATION: (200)
<223> OTHER INFORMATION: Arg, Lys, Met or Ile
<220> FEATURE:
<221> NAME/KEY: MOD_RES
<222> LOCATION: (206)
<223> OTHER INFORMATION: Ala, Gly, Cys, Asp, Glu, Gln, Asn, Ser, Thr or
      Met
<220> FEATURE:
<221> NAME/KEY: MOD_RES
<222> LOCATION: (207)
<223> OTHER INFORMATION: Ala, Gly, Cys, Asp, Asn, Glu or Gln
<220> FEATURE:
<221> NAME/KEY: MOD_RES
<222> LOCATION: (209)
<223> OTHER INFORMATION: Arg, Lys, Met, Ile, Asn, Asp, Glu or Gln
<220> FEATURE:
<221> NAME/KEY: MOD_RES
<222> LOCATION: (211)
<223> OTHER INFORMATION: Leu, Val, Met or Ile
<220> FEATURE:
<221> NAME/KEY: MOD_RES
<222> LOCATION: (212)
<223> OTHER INFORMATION: Phe, Tyr, Thr, His or Trp
<220> FEATURE:
<221> NAME/KEY: MOD_RES
<222> LOCATION: (216)
<223> OTHER INFORMATION: Ile, Val, Leu or Met
<220> FEATURE:
<221> NAME/KEY: MOD_RES
<222> LOCATION: (217)
<223> OTHER INFORMATION: Met, Cys, Ile, Leu, Val, Thr or Ser
<221> NAME/KEY: MOD_RES
<222> LOCATION: (219)
<223> OTHER INFORMATION: Leu, Val, Met, Thr or Ser
<220> FEATURE:
<223> OTHER INFORMATION: each Xaa may also be any amino acid.

<400> SEQUENCE: 21

Cys Gly Pro Gly Arg Gly Xaa Gly Xaa Arg Arg His Pro Lys Lys Leu
```

```
                1               5               10              15
Thr Pro Leu Ala Tyr Lys Gln Phe Ile Pro Asn Val Ala Glu Lys Thr
                        20                  25                  30

Leu Gly Ala Ser Gly Arg Tyr Glu Gly Lys Ile Xaa Arg Asn Ser Glu
            35                  40                  45

Arg Phe Lys Glu Leu Thr Pro Asn Tyr Asn Pro Asp Ile Ile Phe Lys
        50                  55                  60

Asp Glu Glu Asn Thr Gly Ala Asp Arg Leu Met Thr Gln Arg Cys Lys
 65                 70                  75                  80

Asp Lys Leu Asn Xaa Leu Ala Ile Ser Val Met Asn Xaa Trp Pro Gly
                85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
        115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
                180                 185                 190

Lys Asp Leu Xaa Pro Gly Asp Xaa Val Leu Ala Ala Asp Xaa Xaa Gly
            195                 200                 205

Xaa Leu Xaa Xaa Ser Asp Phe Xaa Xaa Phe Xaa Asp Arg
210                 215                 220
```

<210> SEQ ID NO 22
<211> LENGTH: 167
<212> TYPE: PRT
<213> ORGANISM: Artificial Sequence
<220> FEATURE:
<223> OTHER INFORMATION: Description of Artificial Sequence: degenerate
      polypeptide sequence
<220> FEATURE:
<221> NAME/KEY: MOD_RES
<222> LOCATION: (7)
<223> OTHER INFORMATION: Gly, Ala, Val, Leu, Ile, Pro, Phe or Tyr
<220> FEATURE:
<221> NAME/KEY: MOD_RES
<222> LOCATION: (8)
<223> OTHER INFORMATION: Gly, Ala, Val, Leu or Ile
<220> FEATURE:
<221> NAME/KEY: MOD_RES
<222> LOCATION: (9)
<223> OTHER INFORMATION: Gly, Ala, Val, Leu, Ile, Lys, His or Arg
<220> FEATURE:
<221> NAME/KEY: MOD_RES
<222> LOCATION: (12)
<223> OTHER INFORMATION: Lys, Arg or His
<220> FEATURE:
<221> NAME/KEY: MOD_RES
<222> LOCATION: (13)
<223> OTHER INFORMATION: Phe, Trp, Tyr or an amino acid gap
<220> FEATURE:
<221> NAME/KEY: MOD_RES
<222> LOCATION: (14)
<223> OTHER INFORMATION: Gly, Ala, Val, Leu, Ile or an amino acid gap
<220> FEATURE:
<221> NAME/KEY: MOD_RES
<222> LOCATION: (17)
<223> OTHER INFORMATION: Asn, Gln, His, Arg or Lys
<220> FEATURE:
<221> NAME/KEY: MOD_RES -continued

```
<222> LOCATION: (19)
<223> OTHER INFORMATION: Gly, Ala, Val, Leu, Ile, Ser or Thr
<220> FEATURE:
<221> NAME/KEY: MOD_RES
<222> LOCATION: (22)
<223> OTHER INFORMATION: Gly, Ala, Val, Leu, Ile, Ser or Thr
<220> FEATURE:
<221> NAME/KEY: MOD_RES
<222> LOCATION: (27)
<223> OTHER INFORMATION: Gly, Ala, Val, Leu, Ile, Ser or Thr
<220> FEATURE:
<221> NAME/KEY: MOD_RES
<222> LOCATION: (29)
<223> OTHER INFORMATION: Ser, Thr, Gln or Asn
<220> FEATURE:
<221> NAME/KEY: MOD_RES
<222> LOCATION: (30)
<223> OTHER INFORMATION: Met, Cys, Gly, Ala, Val, Leu, Ile, Ser or Thr
<220> FEATURE:
<221> NAME/KEY: MOD_RES
<222> LOCATION: (31)
<223> OTHER INFORMATION: Gly, Ala, Val, Leu, Ile or Pro
<220> FEATURE:
<221> NAME/KEY: MOD_RES
<222> LOCATION: (33)
<223> OTHER INFORMATION: Arg, His or Lys
<220> FEATURE:
<221> NAME/KEY: MOD_RES
<222> LOCATION: (40)
<223> OTHER INFORMATION: Gly, Ala, Val, Leu, Ile, Pro, Arg, His or Lys
<220> FEATURE:
<221> NAME/KEY: MOD_RES
<222> LOCATION: (41)
<223> OTHER INFORMATION: Gly, Ala, Val, Leu, Ile, Phe or Tyr
<220> FEATURE:
<221> NAME/KEY: MOD_RES
<222> LOCATION: (44)
<223> OTHER INFORMATION: Arg, His or Lys
<220> FEATURE:
<221> NAME/KEY: MOD_RES
<222> LOCATION: (45)
<223> OTHER INFORMATION: Gly, Ala, Val, Leu, Ile, Ser or Thr
<220> FEATURE:
<221> NAME/KEY: MOD_RES
<222> LOCATION: (46)
<223> OTHER INFORMATION: Thr or Ser
<220> FEATURE:
<221> NAME/KEY: MOD_RES
<222> LOCATION: (48)
<223> OTHER INFORMATION: Gly, Ala, Val, Leu, Ile, Asn or Gln
<220> FEATURE:
<221> NAME/KEY: MOD_RES
<222> LOCATION: (53)
<223> OTHER INFORMATION: Arg, His or Lys
<220> FEATURE:
<221> NAME/KEY: MOD_RES
<222> LOCATION: (54)
<223> OTHER INFORMATION: Asp or Glu
<220> FEATURE:
<221> NAME/KEY: MOD_RES
<222> LOCATION: (71)
<223> OTHER INFORMATION: Ser or Thr
<220> FEATURE:
<221> NAME/KEY: MOD_RES
<222> LOCATION: (79)
<223> OTHER INFORMATION: Glu, Asp, Gln or Asn
<220> FEATURE:
<221> NAME/KEY: MOD_RES
<222> LOCATION: (83)
<223> OTHER INFORMATION: Glu or Asp
<220> FEATURE:
<221> NAME/KEY: MOD_RES
<222> LOCATION: (84)
<223> OTHER INFORMATION: Arg, His or Lys
<220> FEATURE:
<221> NAME/KEY: MOD_RES
<222> LOCATION: (85)
<223> OTHER INFORMATION: Gly, Ala, Val, Leu or Ile
<220> FEATURE:
```

```
<221> NAME/KEY: MOD_RES
<222> LOCATION: (87)
<223> OTHER INFORMATION: Gly, Ala, Val, Leu, Ile, Thr or Ser
<220> FEATURE:
<221> NAME/KEY: MOD_RES
<222> LOCATION: (95)
<223> OTHER INFORMATION: Met, Cys, Gln, Asn, Arg, Lys or His
<220> FEATURE:
<221> NAME/KEY: MOD_RES
<222> LOCATION: (100)
<223> OTHER INFORMATION: Arg, His or Lys
<220> FEATURE:
<221> NAME/KEY: MOD_RES
<222> LOCATION: (107)
<223> OTHER INFORMATION: Trp, Phe, Tyr, Arg, His or Lys
<220> FEATURE:
<221> NAME/KEY: MOD_RES
<222> LOCATION: (114)
<223> OTHER INFORMATION: Gly, Ala, Val, Leu, Ile, Ser, Thr, Tyr or Phe
<220> FEATURE:
<221> NAME/KEY: MOD_RES
<222> LOCATION: (115)
<223> OTHER INFORMATION: Gln, Asn, Asp or Glu
<220> FEATURE:
<221> NAME/KEY: MOD_RES
<222> LOCATION: (116)
<223> OTHER INFORMATION: Asp or Glu
<220> FEATURE:
<221> NAME/KEY: MOD_RES
<222> LOCATION: (125)
<223> OTHER INFORMATION: Gly, Ala, Val, Leu, or Ile
<220> FEATURE:
<221> NAME/KEY: MOD_RES
<222> LOCATION: (134)
<223> OTHER INFORMATION: Arg, His or Lys
<220> FEATURE:
<221> NAME/KEY: MOD_RES
<222> LOCATION: (135)
<223> OTHER INFORMATION: Asn, Gln, Thr or Ser
<220> FEATURE:
<221> NAME/KEY: MOD_RES
<222> LOCATION: (139)
<223> OTHER INFORMATION: Gly, Ala, Val, Leu, Ile, Ser, Thr, Met or Cys
<220> FEATURE:
<221> NAME/KEY: MOD_RES
<222> LOCATION: (141)
<223> OTHER INFORMATION: Gly, Ala, Val, Leu, Ile, Thr or Ser
<220> FEATURE:
<221> NAME/KEY: MOD_RES
<222> LOCATION: (157)
<223> OTHER INFORMATION: Arg, His or Lys
<220> FEATURE:
<221> NAME/KEY: MOD_RES
<222> LOCATION: (158)
<223> OTHER INFORMATION: Asn, Gln, Gly, Ala, Val, Leu or Ile
<220> FEATURE:
<221> NAME/KEY: MOD_RES
<222> LOCATION: (160)
<223> OTHER INFORMATION: Gly, Ala, Val, Leu or Ile
<220> FEATURE:
<221> NAME/KEY: MOD_RES
<222> LOCATION: (162)
<223> OTHER INFORMATION: Gly, Ala, Val, Leu, Ile, Ser, Thr or Cys
<220> FEATURE:
<221> NAME/KEY: MOD_RES
<222> LOCATION: (166)
<223> OTHER INFORMATION: Gly, Ala, Val, Leu, Ile, Thr or Ser
<221> NAME/KEY: MOD_RES
<222> LOCATION: (167)
<223> OTHER INFORMATION: Asp or Glu
<220> FEATURE:
<223> OTHER INFORMATION: each Xaa may also be any amino acid.

<400> SEQUENCE: 22

Cys Gly Pro Gly Arg Gly Xaa Xaa Xaa Arg Arg Xaa Xaa Xaa Pro Lys
 1               5                  10                  15

Xaa Leu Xaa Pro Leu Xaa Tyr Lys Gln Phe Xaa Pro Xaa Xaa Xaa Glu
```

```
            20                  25                  30
Xaa Thr Leu Gly Ala Ser Gly Xaa Xaa Glu Gly Xaa Xaa Arg Xaa
            35                  40                  45

Ser Glu Arg Phe Xaa Xaa Leu Thr Pro Asn Tyr Asn Pro Asp Ile Ile
 50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
                85                  90                  95

Pro Gly Val Xaa Leu Arg Val Thr Glu Gly Xaa Asp Glu Asp Gly His
                100                 105                 110

His Xaa Xaa Xaa Ser Leu His Tyr Glu Gly Arg Ala Xaa Asp Ile Thr
            115                 120                 125

Thr Ser Asp Arg Asp Xaa Xaa Lys Tyr Gly Xaa Leu Xaa Arg Leu Ala
        130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
            165
```

<210> SEQ ID NO 23
<211> LENGTH: 627
<212> TYPE: DNA
<213> ORGANISM: Homo sapiens
<220> FEATURE:
<221> NAME/KEY: CDS
<222> LOCATION: (1)..(624)

<400> SEQUENCE: 23

```
atg tgg aaa tgg ata ctg aca cat tgt gcc tca gcc ttt ccc cac ctg     48
Met Trp Lys Trp Ile Leu Thr His Cys Ala Ser Ala Phe Pro His Leu
 1               5                  10                  15 ccc ggc tgc tgc tgc tgc ttt ttg ttg ctg ttc ttg gtg tct tcc         96
Pro Gly Cys Cys Cys Cys Phe Leu Leu Leu Phe Leu Val Ser Ser
                20                  25                  30 gtc cct gtc acc tgc caa gcc ctt ggt cag gac atg gtg tca cca gag    144
Val Pro Val Thr Cys Gln Ala Leu Gly Gln Asp Met Val Ser Pro Glu
            35                  40                  45 gcc acc aac tct tct tcc tcc tcc ttc tcc tct cct tcc agc gcg gga    192
Ala Thr Asn Ser Ser Ser Ser Ser Phe Ser Ser Pro Ser Ser Ala Gly
 50                  55                  60 agg cat gtg cgg agc tac aat cac ctt caa gga gat gtc cgc tgg aga    240
Arg His Val Arg Ser Tyr Asn His Leu Gln Gly Asp Val Arg Trp Arg
 65                  70                  75                  80 aag cta ttc tct ttc acc aag tac ttt ctc aag att gag aag aac ggg    288
Lys Leu Phe Ser Phe Thr Lys Tyr Phe Leu Lys Ile Glu Lys Asn Gly
                85                  90                  95 aag gtc agc ggg acc aag aag gag aac tgc ccg tac agc atc ctg gag    336
Lys Val Ser Gly Thr Lys Lys Glu Asn Cys Pro Tyr Ser Ile Leu Glu
                100                 105                 110 ata aca tca gta gaa atc gga gtt gtt gcc gtc aaa gcc att aac agc    384
Ile Thr Ser Val Glu Ile Gly Val Val Ala Val Lys Ala Ile Asn Ser
            115                 120                 125 aac tat tac tta gcc atg aac aag aag ggg aaa ctc tat ggc tca aaa    432
Asn Tyr Tyr Leu Ala Met Asn Lys Lys Gly Lys Leu Tyr Gly Ser Lys
        130                 135                 140 gaa ttt aac aat gac tgt aag ctg aag gag agg ata gag gaa aat gga    480
Glu Phe Asn Asn Asp Cys Lys Leu Lys Glu Arg Ile Glu Glu Asn Gly
145                 150                 155                 160
```

```
tac aat acc tat gca tca ttt aac tgg cag cat aat ggg agg caa atg    528
Tyr Asn Thr Tyr Ala Ser Phe Asn Trp Gln His Asn Gly Arg Gln Met
                165                 170                 175 tat gtg gca ttg aat gga aaa gga gct cca agg aga gga cag aaa aca    576
Tyr Val Ala Leu Asn Gly Lys Gly Ala Pro Arg Arg Gly Gln Lys Thr
            180                 185                 190 cga agg aaa aac acc tct gct cac ttt ctt cca atg gtg gta cac tca    624
Arg Arg Lys Asn Thr Ser Ala His Phe Leu Pro Met Val Val His Ser
        195                 200                 205 tag                                                                 627

<210> SEQ ID NO 24
<211> LENGTH: 208
<212> TYPE: PRT
<213> ORGANISM: Homo sapiens

<400> SEQUENCE: 24

Met Trp Lys Trp Ile Leu Thr His Cys Ala Ser Ala Phe Pro His Leu
 1               5                  10                  15

Pro Gly Cys Cys Cys Cys Cys Phe Leu Leu Leu Phe Leu Val Ser Ser
                20                  25                  30

Val Pro Val Thr Cys Gln Ala Leu Gly Gln Asp Met Val Ser Pro Glu
            35                  40                  45

Ala Thr Asn Ser Ser Ser Ser Phe Ser Ser Pro Ser Ser Ala Gly
        50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205

<210> SEQ ID NO 25
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 25
gcgcgcttcg aagcgaggca gccagcgagg gagagagcga gcgggcgagc cggagcgagg    60
aaatcgatgc gcgc                                                      74

<210> SEQ ID NO 26
<211> LENGTH: 74
```

<212> TYPE: DNA
<213> ORGANISM: Artificial Sequence
<220> FEATURE:
<223> OTHER INFORMATION: Description of Artificial Sequence: primer

<400> SEQUENCE: 26
gcgcgcagat ctgggaaagc gcaagagaga gcgcacacgc acacaccgc cgcgcgcact    60 cgggatccgc gcgc    74

<210> SEQ ID NO 27
<211> LENGTH: 996
<212> TYPE: DNA
<213> ORGANISM: Artificial Sequence
<220> FEATURE:
<223> OTHER INFORMATION: Description of Artificial Sequence: gene
      activation construct

<400> SEQUENCE: 27
cgaagcgagg cagccagcga gggagagagc gagcgggcga gccggagcga ggaaatcgaa    60
ggttcgaatc cttcccccac caccatcact ttcaaaagtc cgaaagaatc tgctccctgc   120
ttgtgtgttg gaggtcgctg agtagtgcgc gagtaaaatt taagctacaa caaggcaagg   180
cttgaccgac aattgcatga agaatctgct tagggttagg cgttttgcgc tgcttcgcga   240
tgtacgggcc agatatacgc gttgacattg attattgact agttattaat agtaatcaat   300 tacgggtca ttagttcata gcccatatat ggagttccgc gttacataac ttacggtaaa   360
tggcccgcct ggctgaccgc ccaacgaccc ccgcccattg acgtcaataa tgacgtatgt   420
tcccatagta acgccaatag ggactttcca ttgacgtcaa tgggtggact atttacggta   480
aactgcccac ttggcagtac atcaagtgta tcatatgcca gtacgccccc ctattgacgt   540
caatgacggt aaatggcccg cctggcatta tgcccagtac atgaccttat gggactttcc   600
tacttggcag tacatctacg tattagtcat cgctattacc atggtgatgc ggttttggca   660
gtacatcaat gggcgtggat agcggtttga ctcacgggga tttccaagtc tccaccccat   720
tgacgtcaat gggagtttgt tttggcacca aaatcaacgg gactttccaa aatgtcgtaa   780
caactccgcc ccattgacgc aaatgggcgg taggcgtgta cggtgggagg tctatataag   840
cagagctctc tggctaacta gagaacccac tgcttactgg cttatcgaaa ttaatacgac   900
tcactatagg gagacccaag cttggtaccg agctcggatc gatctgggaa agcgcaagag   960
agagcgcaca cgcacacacc cgccgcgcgc actcgg   996

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: antisense
      construct

<400> SEQUENCE: 28
gtcctggcgc cgccgccgcc gtcgcc    26

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: antisense
      construct

<400> SEQUENCE: 29

```
ttccgatgac cggcctttcg cggtga                                              26

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: antisense
      construct

<400> SEQUENCE: 30
gtgcacggaa aggtgcaggc cacact                                              26
```